US010034683B2

(12) United States Patent
Monroe et al.

(10) Patent No.: US 10,034,683 B2
(45) Date of Patent: Jul. 31, 2018

(54) ULTRASONIC SURGICAL INSTRUMENT WITH RIGIDIZING ARTICULATION DRIVE MEMBERS

(71) Applicant: Ethicon Endo-Surgery, LLC, Guaynabo, PR (US)

(72) Inventors: David A. Monroe, Milford, OH (US); Richard W. Timm, Cincinnati, OH (US); Craig N. Faller, Batavia, OH (US); Kristen L. Pirozzi, Cincinnati, OH (US); Jacob S. Gee, Cincinnati, OH (US); Jeffrey D. Messerly, Cincinnati, OH (US); John B. Schulte, West Chester, OH (US); Benjamin D. Dickerson, Cincinnati, OH (US); Ryan M. Asher, Cincinnati, OH (US); Cara L. Shapiro, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 385 days.

(21) Appl. No.: 14/688,458

(22) Filed: Apr. 16, 2015

(65) Prior Publication Data

US 2016/0302812 A1 Oct. 20, 2016

(51) Int. Cl.
*A61B 17/295* (2006.01)
*A61B 17/32* (2006.01)
(Continued)

(52) U.S. Cl.
CPC .... *A61B 17/295* (2013.01); *A61B 17/320068* (2013.01); *A61B 17/320092* (2013.01);
(Continued)

(58) Field of Classification Search
CPC .. A61B 17/320092; A61B 2017/00323; A61B 2017/00327; A61B 2017/00314; A61B 2017/2946
See application file for complete search history.

(56) References Cited

U.S. PATENT DOCUMENTS

| | | | |
|---|---|---|---|
| 5,147,380 A | * | 9/1992 | Hernandez ............. A61B 10/06 600/564 |
| 5,322,055 A | | 6/1994 | Davison et al. |

(Continued)

OTHER PUBLICATIONS

U.S. Appl. No. 14/258,179, filed Apr. 22, 2014.
(Continued)

*Primary Examiner* — Alexander Orkin
(74) *Attorney, Agent, or Firm* — Frost Brown Todd LLC

(57) ABSTRACT

A surgical apparatus comprises a body, an ultrasonic transducer, a shaft, an acoustic waveguide, an articulation section, an end effector, and an articulation lock assembly. The ultrasonic transducer is operable to convert electrical power into ultrasonic vibrations. The shaft couples the end effector and the body together. The acoustic waveguide is coupled with the transducer and includes a flexible portion. The articulation section is coupled with the shaft and encompasses the flexible portion of the waveguide. The articulation section comprises a first member and a second member. The second member is longitudinally translatable relative to the first member. The end effector comprises an ultrasonic blade in acoustic communication with the ultrasonic transducer. The articulation lock comprises a tensioning feature, which is configured to selectively apply tension to at least one of the first member and the second member of the articulation section to thereby increase rigidity in the articulation section.

19 Claims, 20 Drawing Sheets

(51) Int. Cl.
  *A61B 17/00* (2006.01)
  *A61B 17/29* (2006.01)
  *A61B 34/00* (2016.01)

(52) U.S. Cl.
  CPC ............. *A61B 2017/003* (2013.01); *A61B 2017/00314* (2013.01); *A61B 2017/00327* (2013.01); *A61B 2017/00389* (2013.01); *A61B 2017/2908* (2013.01); *A61B 2017/2946* (2013.01); *A61B 2034/715* (2016.02)

(56) References Cited

U.S. PATENT DOCUMENTS

| | | | |
|---|---|---|---|
| 5,704,534 A * | 1/1998 | Huitema | A61B 17/07207 227/175.1 |
| 5,766,196 A * | 6/1998 | Griffiths | A61B 17/29 600/564 |
| 5,873,873 A | 2/1999 | Smith et al. | |
| 5,897,523 A | 4/1999 | Wright et al. | |
| 5,980,510 A | 11/1999 | Tsonton et al. | |
| 5,989,264 A | 11/1999 | Wright | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,621,930 B2 | 11/2009 | Houser | |
| 8,100,824 B2 | 1/2012 | Hegeman et al. | |
| 8,105,350 B2 | 1/2012 | Lee et al. | |
| 8,461,744 B2 | 6/2013 | Wiener et al. | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,095,367 B2 | 8/2015 | Olson et al. | |
| 2003/0036748 A1* | 2/2003 | Cooper | A61B 17/00234 606/1 |
| 2005/0107667 A1* | 5/2005 | Danitz | A61B 1/0053 600/139 |
| 2005/0273084 A1* | 12/2005 | Hinman | A61B 1/008 606/1 |
| 2006/0079874 A1 | 4/2006 | Faller et al. | |
| 2006/0178562 A1* | 8/2006 | Saadat | A61B 1/0055 600/142 |
| 2006/0264787 A1* | 11/2006 | Yamada | A61B 17/32006 601/2 |
| 2007/0191713 A1 | 8/2007 | Eichmann et al. | |
| 2007/0219550 A1 | 9/2007 | Thompson et al. | |
| 2007/0282333 A1 | 12/2007 | Fortson et al. | |
| 2008/0200940 A1 | 8/2008 | Eichmann et al. | |
| 2012/0078247 A1 | 3/2012 | Worrell et al. | |
| 2012/0112687 A1 | 5/2012 | Houser et al. | |
| 2012/0116265 A1 | 5/2012 | Houser et al. | |
| 2014/0005701 A1 | 1/2014 | Olson et al. | |
| 2014/0005703 A1 | 1/2014 | Stulen et al. | |
| 2015/0080924 A1 | 3/2015 | Stulen et al. | |

OTHER PUBLICATIONS

U.S. Appl. No. 61/410,603, filed Nov. 5, 2010.
International Search Report and Written Opinion dated Oct. 20, 2016 re Application No. PCT/US16/27680.

* cited by examiner

ULTRASONIC SURGICAL INSTRUMENT
WITH RIGIDIZING ARTICULATION DRIVE
MEMBERS

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, now U.S. Pat. No. 8,623,027, issued Jan. 7, 2014, the disclosure of which is incorporated by reference herein; U.S. Pub. No. 2010/0069940, entitled "Ultrasonic Device for Fingertip Control," published Mar. 18, 2010, now U.S. Pat. No. 9,023,071, issued May 5, 2015, the disclosure of which is incorporated by reference herein; and U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and U.S. Pub. No. 2012/0029546, entitled "Ultrasonic Surgical Instrument Blades," published Feb. 2, 2012, now U.S. Pat. No. 8,591,536, issued Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, now U.S. Pat. No. 9,381,058, issued Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," now U.S. Pat. No. 9,393,037, issued Jul. 19, 2016 the disclosure of which is incorporated by reference herein; U.S. Pub. No. 2014/0005703, entitled "Surgical Instruments with Articulating Shafts," published Jan. 2, 2014, now U.S. Pat. No. 9,408,622, issued Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, now U.S. Pat. No. 9,095,367, issued Aug. 4, 2015, the disclosure of which is incorporated by reference herein; U.S. Pub. No. 2015/0080924, entitled ""Articulation Features for Ultrasonic Surgical Instrument," published Mar. 19, 2015, the disclosure of which is incorporated by reference herein; and U.S. patent application Ser. No. 14/258,179, entitled Ultrasonic Surgical Device with Articulating End Effector," filed Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
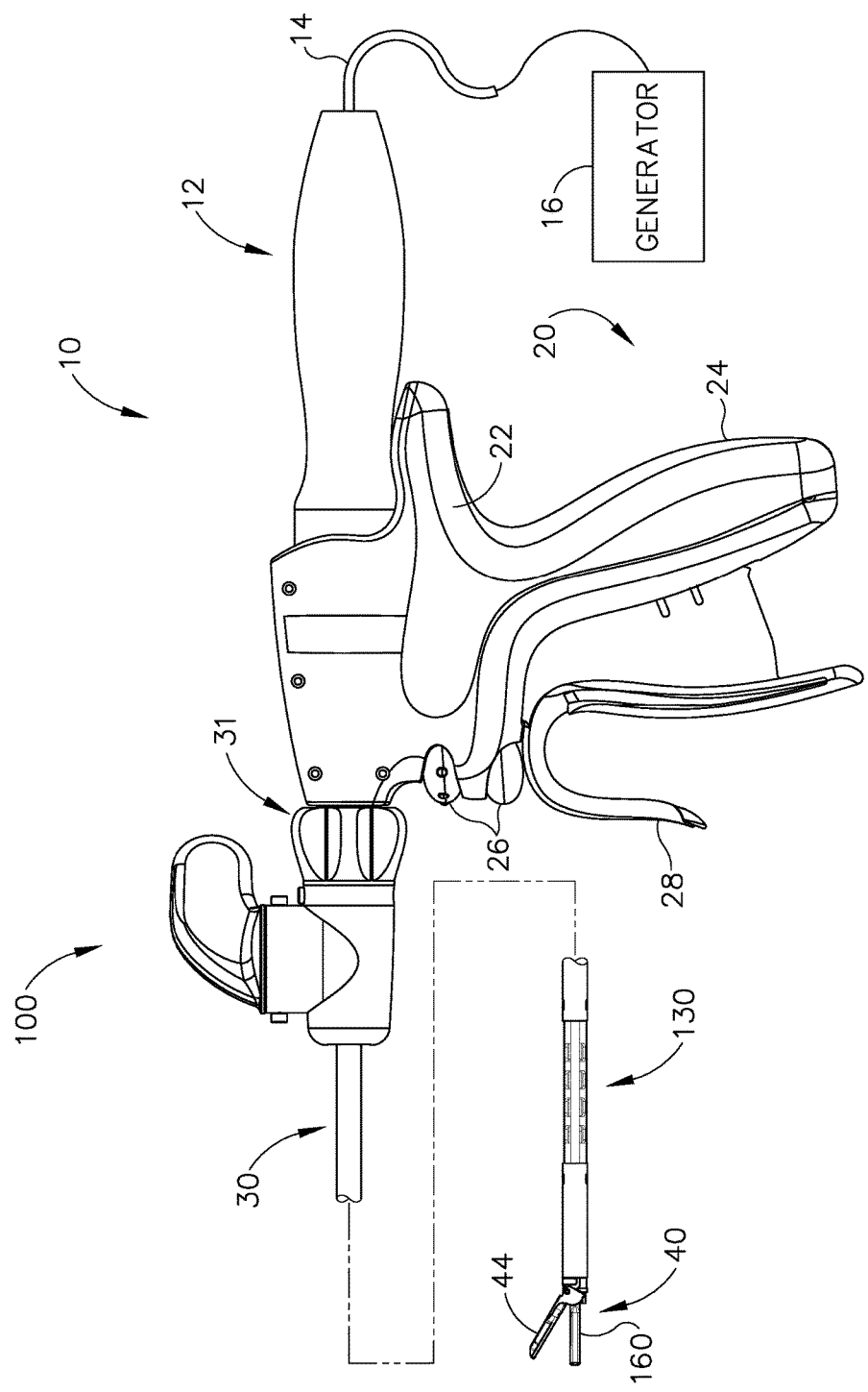
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. EXEMPLARY ULTRASONIC SURGICAL INSTRUMENT

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
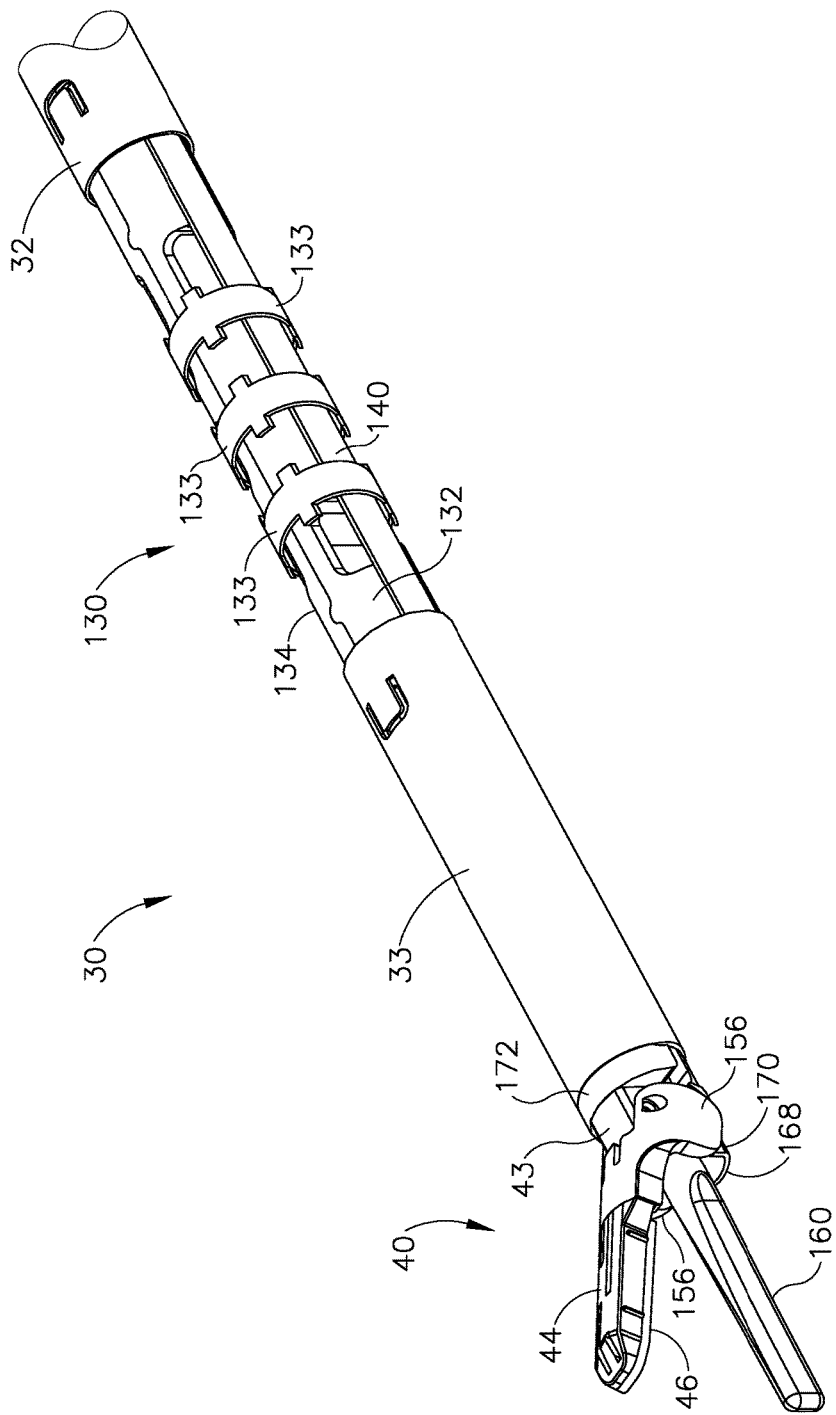
FIG. 2 depicts a perspective view of an articulation section of a shaft assembly and an end effector of the surgical instrument of FIG. 1.
Figure 3:
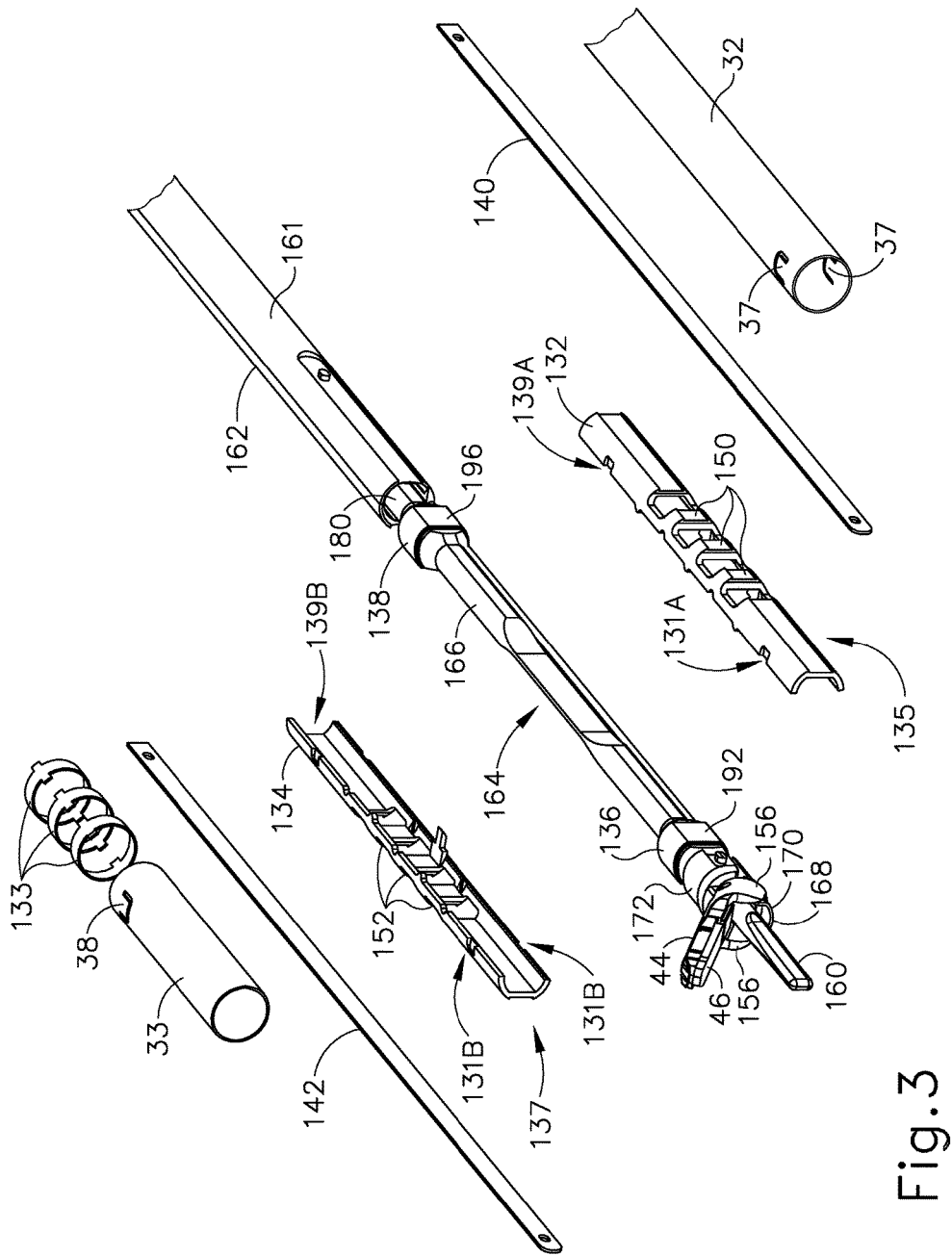
FIG. 3 depicts an exploded perspective view of an articulation section of the shaft assembly of FIG. 2.
Figure 4:
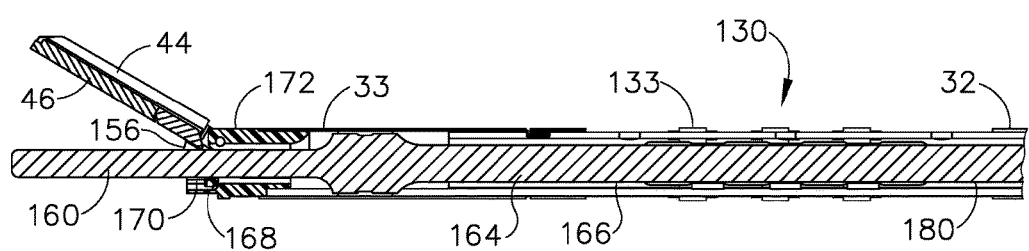
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

In some examples a cable (not shown) may be secured to lower distal shaft element (170). Such a cable may be operable to translate longitudinally relative to an articulation section (130) of shaft assembly (30) to selectively pivot clamp arm (44) toward and away from blade (160). In further examples, the cable is coupled with trigger (28) such that the cable translates proximally in response to pivoting of trigger (28) toward pistol grip (24), and such that clamp arm (44) thereby pivots toward blade (160) in response to pivoting of trigger (28) toward pistol grip (24). In addition, the cable may translate distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, now U.S. Pat. No. 9,393,037, and/or U.S. Pub. No. 2014/0114334, now U.S. Pat. No. 9,095,367, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-6B, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, now U.S. Pat. No. 9,402,682, issued Aug. 2, 2016, the disclosure of which is incorporated by reference herein. As another merely illustrative example, articulation section (130) may be configured in accordance with one or more teachings of U.S. Pub. No. 2014/0005701, now U.S. Pat. No. 9,393,037 and/or U.S. Pub. No. 2014/0114334, now U.S. Pat. No. 9,095,367, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
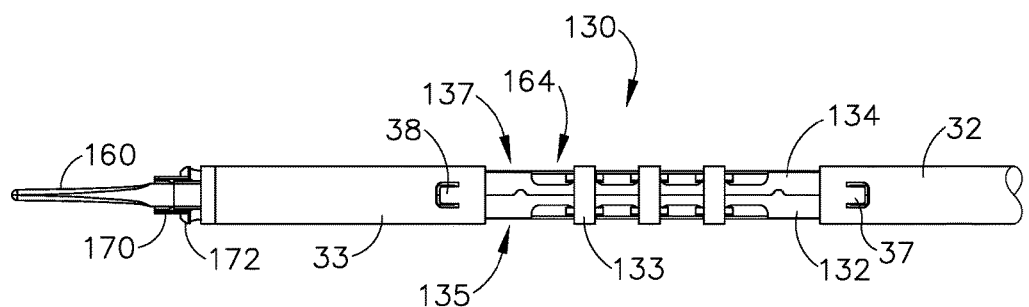
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
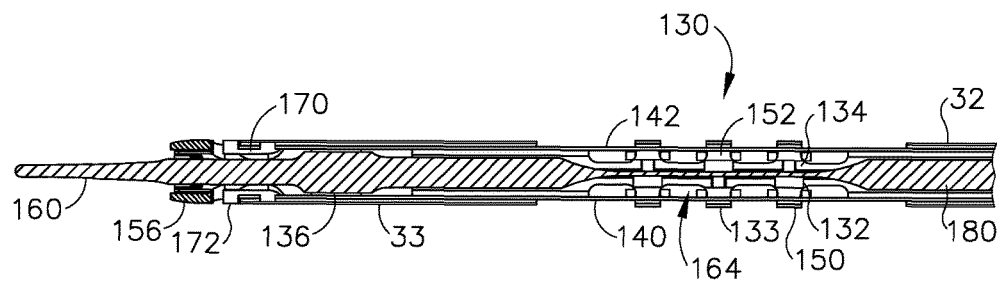
FIG. 6A depicts a cross-sectional top view of the shaft assembly and end effector of FIG. 2 in a straight configuration.
Figure 6B:
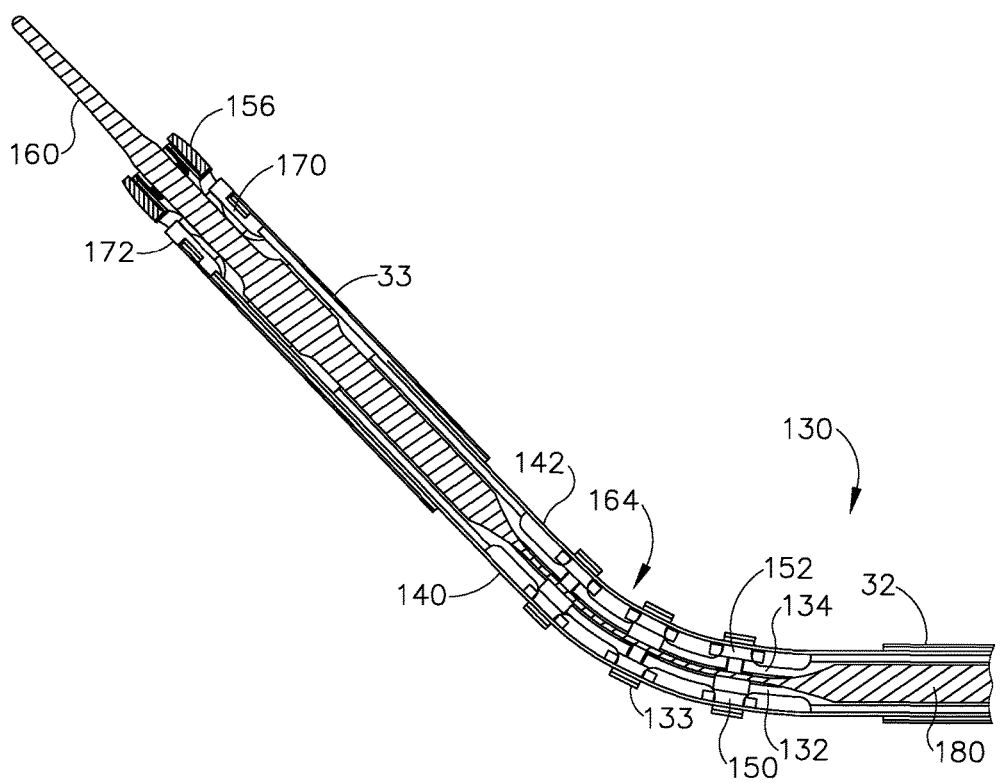
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," published Oct. 31, 2013, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 7:
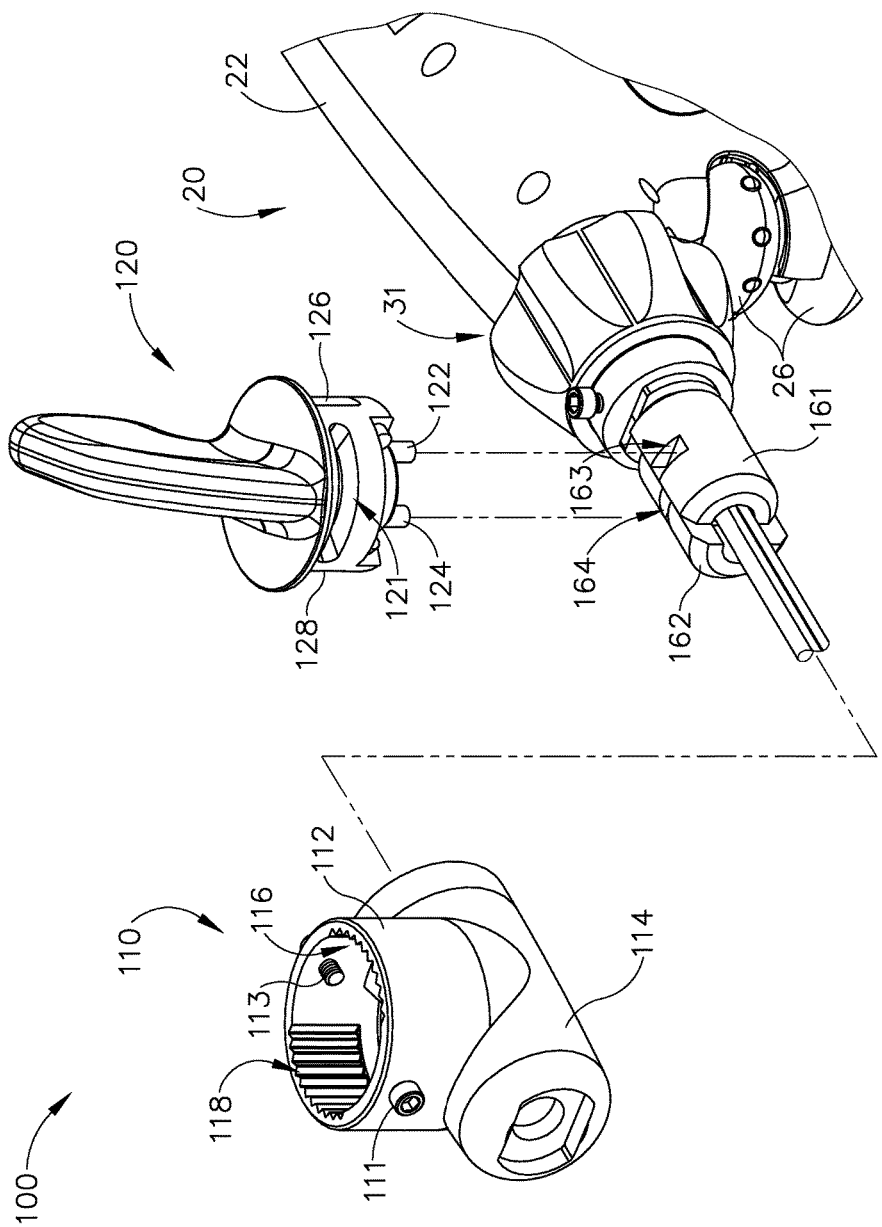
FIG. 7 depicts a partially exploded perspective view of an articulation control assembly of the instrument of FIG. 1.
Figure 8:
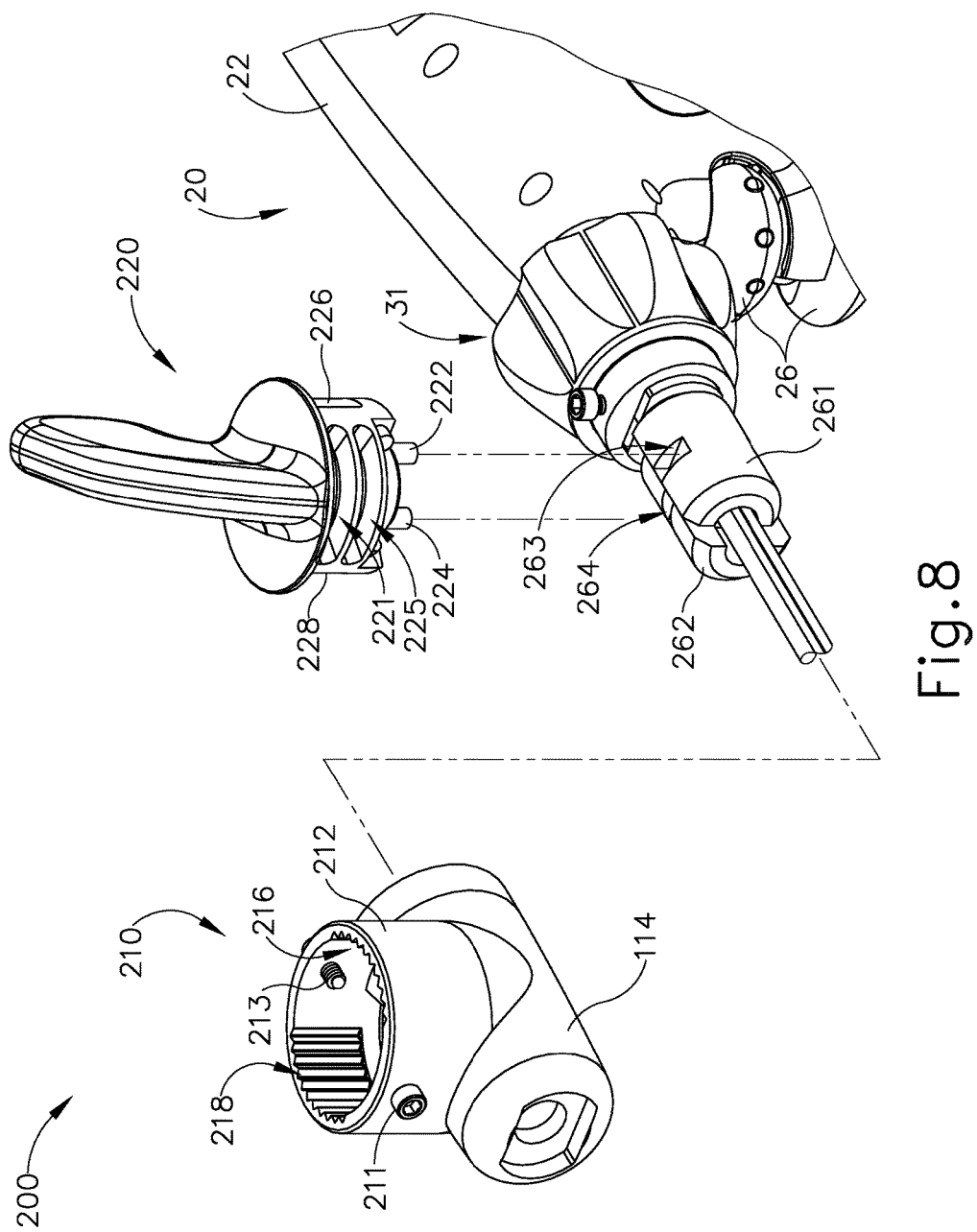
FIG. 8 depicts a partially exploded perspective view of an exemplary alternative articulation control assembly that may be incorporated into the instrument of FIG. 1.

As best seen in FIG. 7, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section (130).

Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

II. EXEMPLARY FEATURES TO PROVIDE RIGIDIZATION OF ARTICULATION SECTION

In some examples it may be desirable to include various features to selectively increase the rigidity of an articulation section, such as articulation section (130) described above. For instance, because of various factors such as manufacturing tolerances, design limitations, material limitations, and/or other factors, articulation sections of some examples may be susceptible to some "play" or other small movement of the articulation section despite being relatively fixed in a given position, such that the articulation section is not entirely rigid. It may be desirable to reduce or eliminate such play in the articulation section, particularly when the articulation section is in a straight, non-articulated configuration. In some examples, such play may be reduced or eliminated by including features for selectively increasing tension in one or two articulation bands similar to articulation bands (140, 142) described above. Such features may reduce or eliminate play in the articulation section because the increased tension in the articulation bands may cause the components of the articulation section to longitudinally compress, thereby increasing the rigidity of the articulation section. It may be desirable to provide control of such features via the handle assembly and/or via the shaft assembly because such positioning may provide enhanced usability, ergonomics, and/or functionality.

In some versions, one or more resilient members resiliently bias articulation bands (140, 142) proximally in order to increase tension in articulation bands (140, 142). Various suitable ways in which one or more resilient members may be used to resiliently bias articulation bands (140, 142) proximally will be apparent to those of ordinary skill in the art in view of the teachings herein. Various examples of features that are configured to selectively increase tension in articulation bands are described in greater detail below. In some examples, tension is selectively increased in one articulation band (140, 142) in order to effectively ridigize the articulation section. In some other examples, tension is selectively increased in both articulation bands (140, 142) simultaneously in order to effectively ridigize the articulation section. Various other examples will be apparent to those of ordinary skill in the art in view of to the teachings herein.

A. Exemplary Alternative Articulation Control Assembly with Rigidizing Cam Feature FIGS. 8-11 show an exemplary alternative articulation control assembly (200) that may be readily incorporated into instrument (10). Except as otherwise noted herein, it should be understood that articulation control assembly (200) is substantially the same as articulation control assembly (100) described above. In particular, as similarly described above, articulation control assembly (200) comprises a housing (210) and a rotatable knob (220). Like with housing (110) described above, housing (210) of the present example comprises a pair of perpendicularly intersecting cylindrical portions (212, 214). Similarly, like knob (120), knob (220) is rotatably disposed within a first hollow cylindrical portion (212) of housing (210) such that knob (220) is operable to rotate within cylindrical portion (212) of housing (210).

Shaft assembly (30) is similarly slidably and rotatably disposed within a second cylindrical portion (214). Shaft assembly (30) comprises a pair of translatable members (261, 262), both of which extend slidably and longitudinally through the proximal portion of outer sheath (32). Translatable members (261, 262) are each longitudinally translatable within second cylindrical portion (214) between a distal position and a proximal position. Like with translatable member (161, 162) described above, translatable members (261, 262) are mechanically coupled with respective articulation bands (140, 142) such that longitudinal translation of translatable member (261) causes longitudinal translation of articulation band (140), and such that longitudinal translation of translatable member (262) causes longitudinal translation of articulation band (142).

Figure 9:
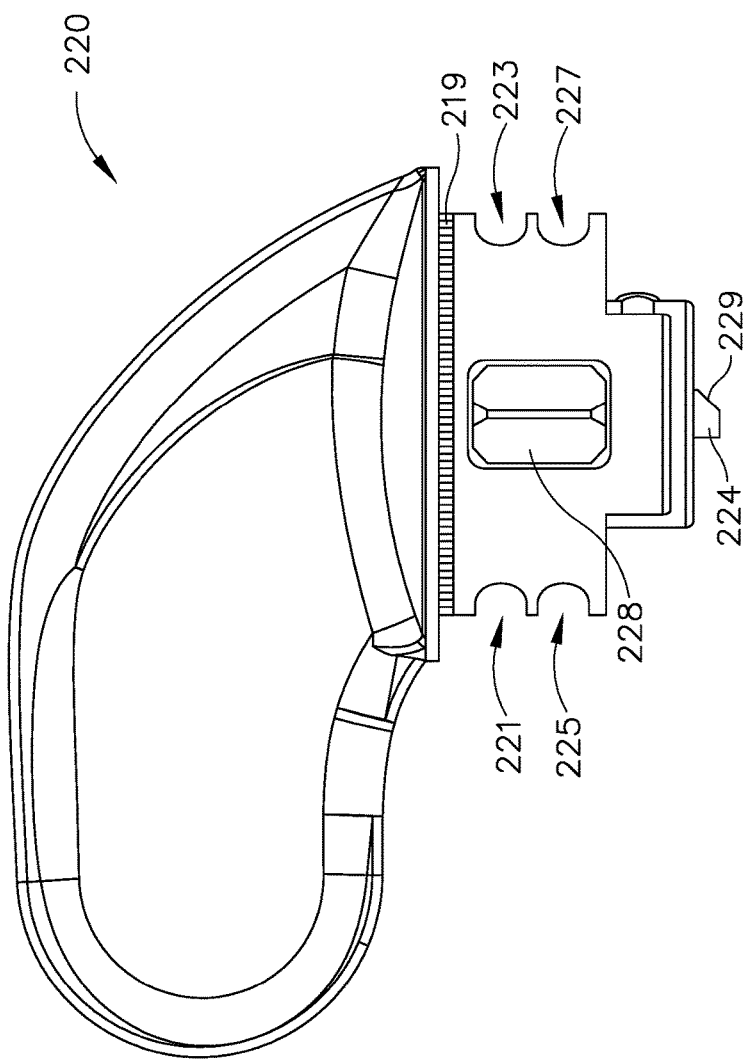
FIG. 9 depicts a side elevational view of a rotatable knob of the articulation control assembly of FIG. 8.
Figure 10:
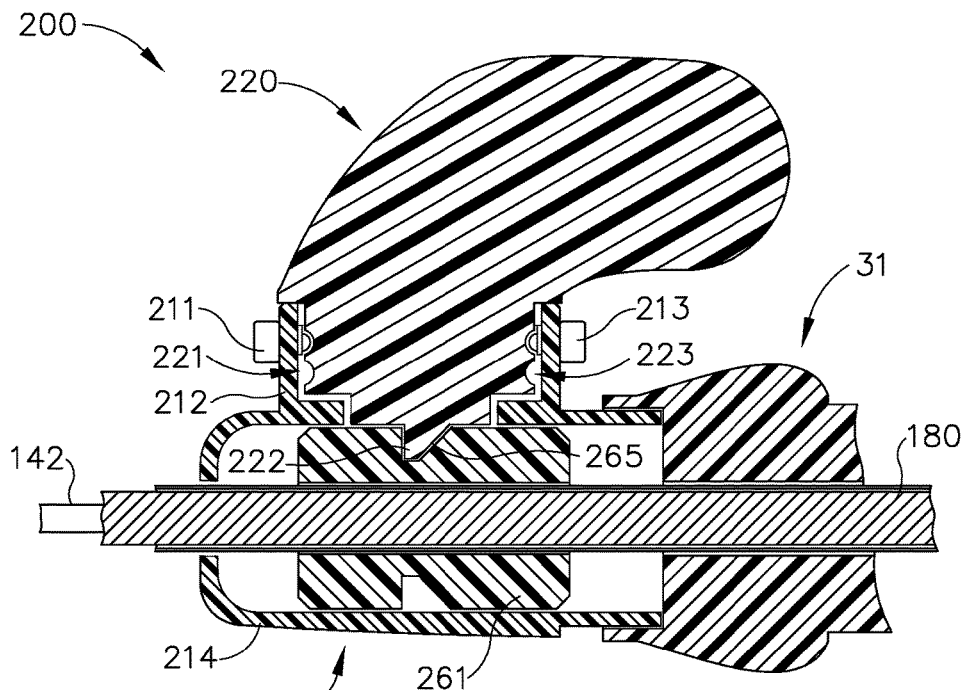
FIG. 10 depicts a cross-sectional side view of the articulation control assembly of FIG. 8, with the knob in a first position.
Figure 11:
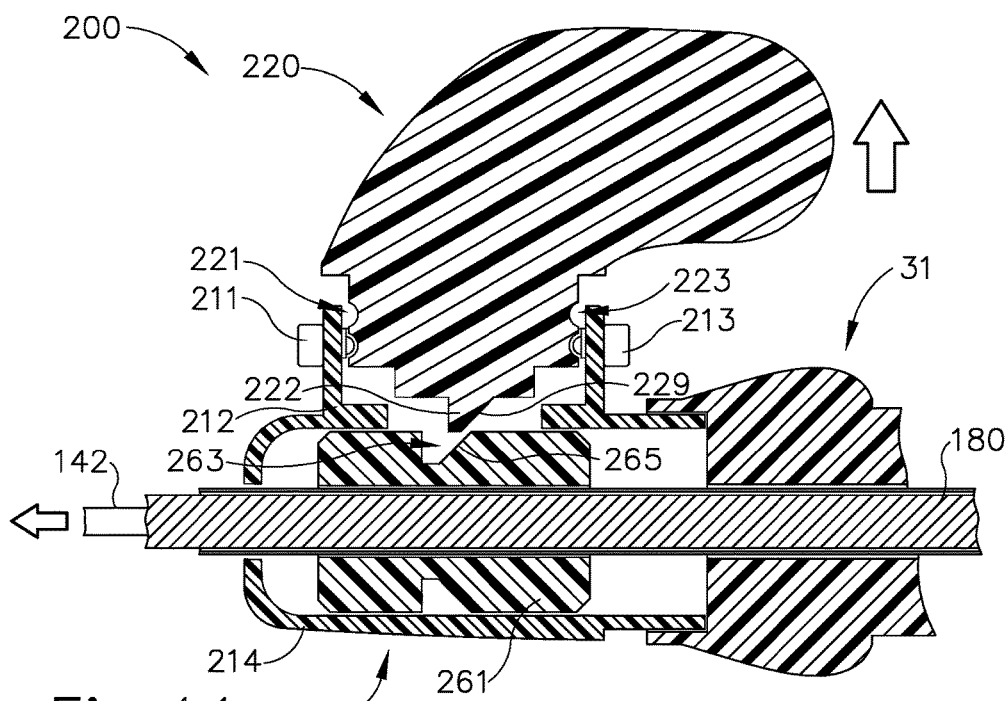
FIG. 11 depicts another side cross-sectional view of the articulation control assembly of FIG. 8, with the knob in a second position.

Knob (220) comprises a pair of pins (222, 224) extending downwardly from a bottom surface of knob (220). Pins (222, 224) extend into second cylindrical portion (214) of housing (210) and are rotatably and slidably disposed within a respective pair of channels (263, 264) formed in top surfaces of translatable members (261, 262). However, unlike pins (122, 124), pins (222, 224) of the present example each include a cam surface (229) on the proximal side of each pin (222, 224), as best seen in FIGS. 9-11. As will be described in greater detail below, each cam surface (229) is configured to engage channels (263, 264) of translatable members (261, 262) to selectively drive translatable members (261, 262) proximally.

Channels (263, 264), like channels (163, 164) described above, are positioned on opposite sides of an axis of rotation of knob (220), such that rotation of knob (220) about that axis causes opposing longitudinal translation of translatable members (261, 262). For instance, rotation of knob (220) in a first direction causes distal longitudinal translation of translatable member (261) and articulation band (140), while simultaneously causing proximal longitudinal translation of translatable member (262) and articulation band (142). Rotation of knob (220) in a second direction causes proximal longitudinal translation of translatable member (261) and articulation band (140), while simultaneously causing distal longitudinal translation of translatable member (262) and articulation band (142). Thus, it should be understood that rotation of knob (220) causes articulation of articulation section (130) as previously described with respect to instrument (10).

Unlike housing (110) described above, housing (210) of the present example comprises a pair of detent features (211, 213) extending inwardly from an interior surface of first cylindrical portion (212). Although detent features (211, 213) of the present example are shown as ball and spring detents, it should be understood that any other suitable detent feature may be used. With knob (220) rotatably disposed within first cylindrical portion (212) of housing (210), detent features (211, 213) are configured to permit knob (220) to be selectively repositioned such that detent features (211, 213) may be disposed within a pair of first arcuate channels (221, 223) or a pair of second arcuate channels (225, 227) formed in knob (220). Thus, it should be understood that rotation of knob (220) will be limited by movement of detent features (211, 213) within channels (221, 223, 225, 227). Detent features (211, 213) also retain knob (220) in housing (210), while permitting knob (220) to be selectively positioned between a first vertical position and a second vertical position within first cylindrical portion (212) of housing (210).

Like with first cylindrical portion (112) described above, an interior surface of first cylindrical portion (212) of the present example further comprises a first angular array of teeth (216) and a second angular array of teeth (218) formed in an interior surface of first cylindrical portion (212). Rotatable knob (220) comprises a pair of outwardly extending engagement members (226, 228) that are configured to engage teeth (216, 218) of first cylindrical portion (212) in a detent relationship to thereby selectively lock knob (220) in a given rotational position. The engagement of engagement members (226, 228) with teeth (216, 218) may be overcome by a user applying sufficient rotational force to knob (220); but absent such force, the engagement will suffice to maintain the straight or articulated configuration of articulation section (230). It should therefore be understood that the ability to selectively lock knob (220) in a particular rotational position will enable an operator to selectively lock articulation section (230) in a particular deflected position relative to the longitudinal axis defined by outer sheath (32).

FIGS. 10 and 11 show an exemplary use of articulation control assembly (200). As can be seen in FIG. 10, articulation control assembly (200) may be initially configured such that knob (220) is in the first vertical position. It should be understood that in the present example the first position of knob (220) corresponds to articulation bands (140, 142) being in high tension to thereby increase the rigidity of articulation section (130). In particular, cam surface (229) of each pin (222, 224) fully engages a corresponding cam surface (265) of each channel (263, 264) in each translatable member (261, 262). Engagement bet between each cam surface (229, 265) causes translatable member (261, 262) to be driven proximally relative to knob (220) thereby increasing articulation bands (140, 142). Such a tension in articulation bands (140, 142) may take up any slack that might otherwise exist in articulation section (130), thereby increasing rigidity in articulation section (130) because such tension places articulation section (130) in compression. It should be understood that it may be desirable to only move knob (220) to the vertical position shown in FIG. 10 when articulation section (130) is in a straight, non-articulated configuration.

Detent features (211, 213) maintain knob (220) in the first position because detent features (211, 213) resiliently engage arcuate channels (221, 223) of knob (220). To articulate articulation section (130) an operator will first have to decrease the rigidity of articulation section (130). When an operator desires to decrease the rigidity of articulation section (130), an operator may transition knob (220) to the second vertical position as seen in FIG. 11. To transition knob (220) to the second position, an operator may apply an upward force to knob (220) by pulling upwardly on knob (220) while holding housing (210) stationary. Such an upward force should be sufficient to overcome the resiliency of detent features (211, 213) to thereby disengage detent features from arcuate channels (221, 223). Once detent features (211, 213) are disengaged from arcuate channels (221, 223) further upward movement of knob (220) will cause detent features to engage arcuate channels (225, 227) to thereby lock knob (220) in the second vertical position as shown in FIG. 11.

Once knob (220) is in the second vertical position, the tension in articulation bands (140, 142) is released and articulation section (130) is in a configuration for articulation. In particular, as can be seen in FIG. 11, knob (220) is positioned relative to each translatable member (261, 262) such that cam surface (229) of each pin (222, 224) only partially engages the corresponding cam surface (265) defined by each translatable member (261, 262). Such engagement may permit each translatable member (261, 262) to translate distally thereby reducing the tension in articulation bands (140, 142).

When knob (220) is in the second position, such a positioning may be visually indicated by an indicator (219) on knob (220). In the present example, indicator (219) (as seen in FIG. 9) is shown as a red stripe around the exterior of knob (220). When knob (220) is in the first position, indicator (219) is covered by cylindrical portion (212) of housing (210) and is thereby obscured from view. Yet in the second position, indicator (219) is visible because knob (220) is in a higher vertical position relative to housing (210), such that indicator (219) is exposed. Although indicator (219) is shown as a red stripe in the present example, it should be understood in other examples, any other color or any other type of indicator may be used.

With rotation knob (220) in the second position, an operator may articulate articulation section (130) by applying a rotational force to knob (220) to thereby rotate knob (220). As rotation knob (220) is rotated, pins (222, 224) drive translatable members (261, 262) in opposing directions as described above thereby articulating articulation section (130). Once articulation section (130) is articulated to a desired position, an operator may cease rotation of knob (220). In some versions, if an operator desires to increase the rigidity of articulation section (130) once articulation section (130) is in the desired position, an operator may force knob (220) downwardly to the first position as described above in order to effectively ridigize articulation section (130). In some other versions, articulation section (130) may only be rigidized by forcing knob (220) downwardly to the second vertical position when articulation section (130) is in a straight, non-articulated configuration.

Figure 12:
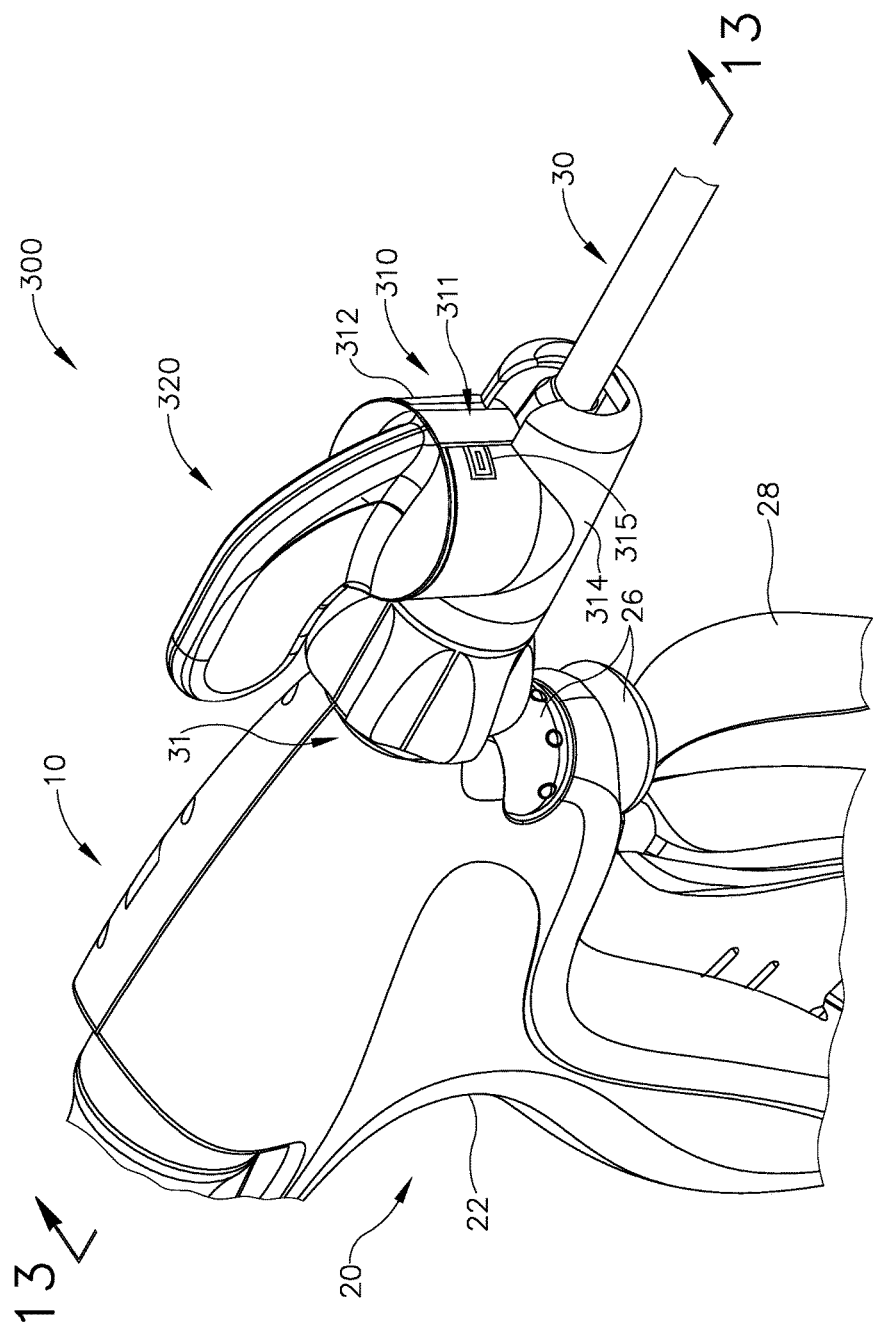
FIG. 12 depicts a perspective view of another exemplary alternative articulation control assembly that may be incorporated into the instrument of FIG. 1.
Figure 13:
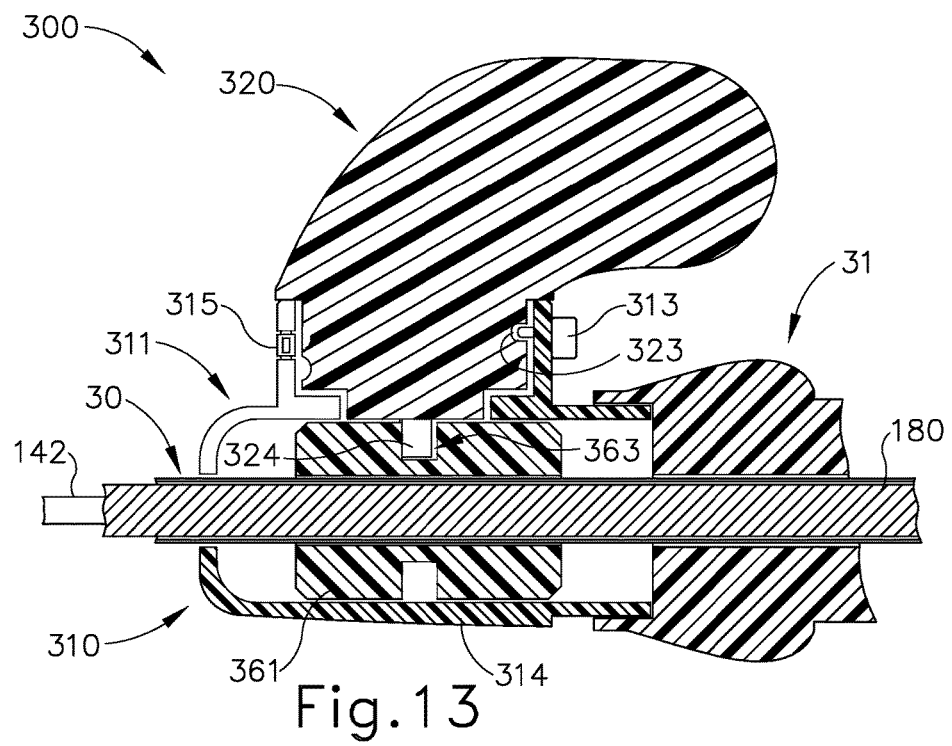
FIG. 13 depicts a cross-sectional side view of the articulation control assembly of FIG. 12, with the cross-section taken along line 13-13 of FIG. 12, with a rotatable knob in a first position.
Figure 14:
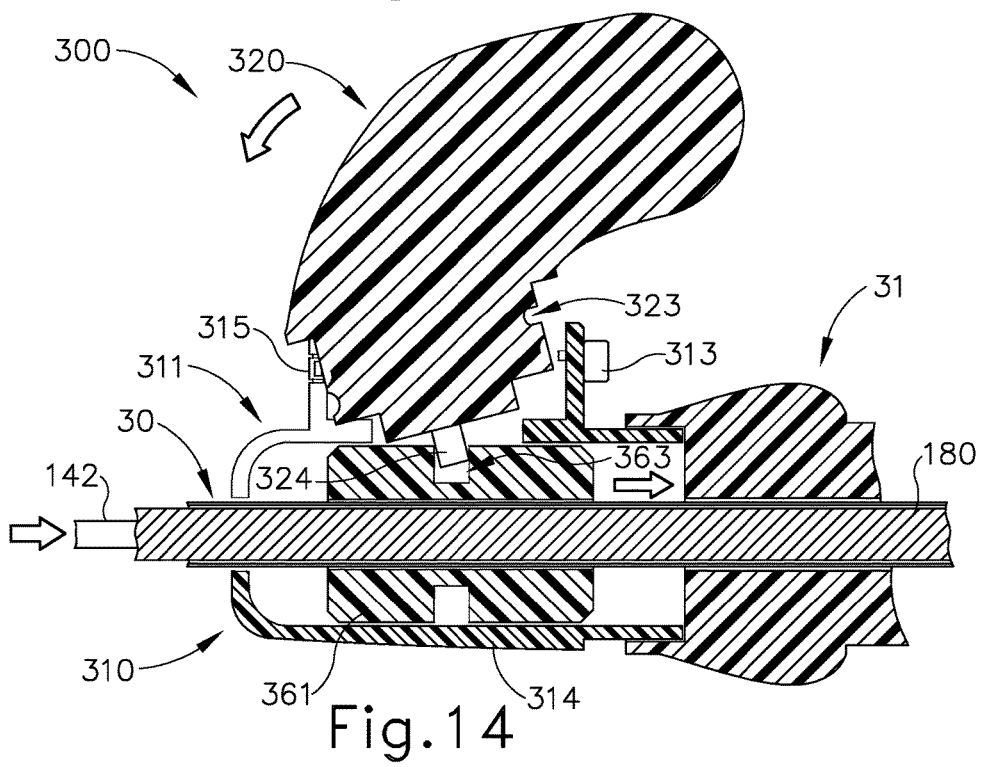
FIG. 14 depicts another cross-sectional side view of the articulation control assembly of FIG. 12, with the cross-section taken along line 13-13 of FIG. 12, with the rotatable knob pivoted to a second position.

B. Exemplary Alternative Articulation Control Assembly with Pivoting Rotatable Knob FIGS. 12-14 show an exemplary alternative articulation control assembly (300) that may be readily incorporated into instrument (10). Except as otherwise noted herein, it should be understood that articulation control assembly (300) is substantially the same as articulation control assembly (100) described above. In particular, as similarly described above, articulation control assembly (300) comprises a housing (310) and a rotatable knob (320). Like with housing (110) described above, housing (310) of the present example comprises a pair of perpendicularly intersecting cylindrical portions (312, 314). Similarly, like knob (120), knob (320) is rotatably disposed within a first hollow cylindrical portion (312) of housing (310) such that knob (320) is operable to rotate within cylindrical portion (312) of housing (310).

Shaft assembly (30) is similarly slidably and rotatably disposed within a second cylindrical portion (314). As can best be seen in FIG. 13, shaft assembly (30) comprises a pair of translatable members (361) (though only a single translatable member is shown), both of which extend slidably and longitudinally through the proximal portion of outer sheath (32). Translatable members (361) are each longitudinally translatable within second cylindrical portion (314) between a distal position and a proximal position. Like with translatable members (161, 162) described above, translatable members (361) are mechanically coupled with respective articulation bands (140, 142) such that longitudinal translation of translatable member (361) causes longitudinal translation of articulation band (140), and such that longitudinal translation of the other translatable member (not shown) causes longitudinal translation of articulation band (142).

Knob (320) comprises a pair of pins (324) (though only a single pin is shown) extending downwardly from a bottom surface of knob (320). Pins (324) extend into second cylindrical portion (314) of housing (310) and are rotatably and slidably disposed within a respective pair of channels (363) (though only a single channel is shown) formed in top surfaces of translatable members (361). Channels (363), like channels (163, 164) described above, are positioned on opposite sides of an axis of rotation of knob (320), such that rotation of knob (320) about that axis causes opposing longitudinal translation of translatable members (361). For instance, rotation of knob (320) in a first direction causes distal longitudinal translation of translatable member (361) and articulation band (140), while simultaneously causing proximal longitudinal translation of translatable member and articulation band (142). Rotation of knob (320) in a second direction causes proximal longitudinal translation of translatable member (361) and articulation band (140), while simultaneously causing distal longitudinal translation of translatable member and articulation band (142). Thus, it should be understood that rotation of knob (320) causes articulation of articulation section (130) a previously described with respect to instrument (10).

Unlike housing (110) described above, housing (310) of the present example comprises a single set screw (313) extending inwardly from an interior surface of first cylindrical portion (312). With knob (320) rotatably disposed within first cylindrical portion (312) of housing (310), set screw (313) is slidably disposed within an arcuate channel (323) formed in knob (320). Thus, it should be understood that rotation of knob (320) will be limited by movement of set screws (313) within channel (323). Set screw (313) also retain knob (320) in housing (310), preventing knob (320) from traveling vertically within first cylindrical portion (312) of housing (310).

Housing (310) further includes an open portion (311). As can best be seen in FIG. 12, open portion (311) is disposed on the distal face of housing (310) and is formed as a vertically extending channel that interrupts the circumference of cylindrical portion (312). Generally, open portion (311) is configured to permit at least a portion of knob (320) to pass distally through housing (310). As will be described in greater detail below, open portion (311) is configured to permit passage of at least a portion of knob (320) because such a feature permits at least a portion of knob (320) to be pivotable relative to housing (310). A knob lock (315) is disposed adjacent to open portion (311). Knob lock (315) is configured to selectively lock and unlock pivoting of knob (320) by selectively closing at least a portion of open portion (311) or otherwise engaging knob (320) to prevent pivoting. By way of example only, knob lock (315) may comprise a "C" shaped member that selectively rotates about cylindrical portion (312) to selectively close off or open the open portion (311) of cylindrical portion (312). As another merely illustrative example, knob lock (315) may comprise a protrusion that selectively extends into or over a portion of open portion (311). Various suitable ways in which a knob lock (315) may be configured and operable will be apparent to those of ordinary skill in the art in view of the teachings herein.

Like with first cylindrical portion (112) described above, an interior surface of first cylindrical portion (312) of the present example comprises a first angular array of teeth (not shown) and a second angular array of teeth (not shown) formed in an interior surface of first cylindrical portion (312). Likewise, knob (320) comprises a pair of outwardly extending engagement members (not shown) that are configured to engage the teeth of first cylindrical portion (312) in a detent relationship to thereby selectively lock knob (320) in a given rotational position. The engagement of the engagement members with the teeth may be overcome by a user applying sufficient rotational force to knob (320); but absent such force, the engagement will suffice to maintain the straight or articulated configuration of articulation section (330). It should therefore be understood that the ability to selectively lock knob (320) in a particular rotational position lock will enable an operator to selectively lock articulation section (330) in a particular deflected position relative to the longitudinal axis defined by outer sheath (32).

FIGS. 13 and 14 show an exemplary use of articulation control assembly (200) to selectively stiffen articulation section (130). It should be understood that in some examples it may be desirable to pivot articulation control assembly (200) to selectively stiffen articulation section (130) because such a feature may improve usability and/or ergonomics. As can be seen in FIG. 13, articulation control assembly (300) may be initially configured such that knob (320) is in a first pivotal position. It should be understood that in the present example the first pivotal position of knob (320) corresponds to articulation bands (140, 142) being relatively relaxed to such that articulation bands (140, 142) are in a configuration for articulating articulation section (130). Further, the first pivotal position corresponds to knob (320) being seated within first cylindrical portion (312) of housing (310). Thus, knob (320) is positioned to rotate within first cylindrical position (312) about a rotation axis to opposingly drive translatable members (361) via pins (324). Accordingly, an operator may rotate knob (320) about the rotation axis while knob (320) is in the first pivotal position in order to articulate articulation section (130). Additionally, to maintain knob (320) within first cylindrical portion (312) while the articulation feature is in use, an operator may optionally engage knob lock (315) in a locked position.

Once an operator desires to increase the rigidity of articulation section (130), an operator may first transition knob lock (315) to an unlocked position to thereby permit pivotal motion of knob (320) about a pivot axis. In this example, the pivot axis is perpendicular to the rotation axis of knob (320) and offset from the rotation axis of knob (320). The pivot axis is also perpendicular to the longitudinal axis of shaft assembly (30) and offset from the longitudinal axis of shaft assembly (30). In particular, in the views shown in FIGS. 13-14, the pivot axis runs into and out of the page, the rotation axis runs vertically between the top of the view and the bottom of the view, and the longitudinal axis runs horizontally between the sides of the view. Once knob lock (315) is in the unlocked position, at least a portion of knob (320) is permitted to pass through open portion (311) of housing (310). To increase the rigidity of articulation section (130) an operator may next apply a horizontal force to knob (320) (e.g., to the left-hand side of the view shown in FIGS. 13-14) while holding housing (310) stationary. Such a horizontal force acting on knob (320) may begin to pivot knob (320) about the pivot axis toward the position shown in FIG. 14.

The above described pivoting of knob (320) may be provided and carried out in numerous different ways. For instance, in some examples knob (320) is comprised of three separate components—a pivoting member, and two side members. In such an example, the pivoting member is be secured to each of the side members by a shaft suitable for pivoting the pivoting member relative to the two side members. In other examples, first cylindrical portion (312) may be equipped with a hinge member or other feature that may be equipped to permit both knob (320) and first cylindrical portion (312) to pivot relative to second cylindrical portion (314). Alternative, any other suitable mechanism for pivoting knob (320) may be used as will be apparent to those of ordinary skill in the art in view of the teachings herein.

Regardless of the particular mechanism for pivoting knob (320), it should be understood that as knob (320) is pivoted, the pivoting action generally applies tension to articulation bands (140, 142) via pins (324) and translatable members (361), thereby increasing the rigidity of articulation section (130). In particular, the pivoting of knob (320) causes pins (324) to move about the pivot axis. As pins (324) move, pins (324) engage a proximal portion of each translatable member (361) such that further movement of pins (324) will simultaneously drive each translatable member (361) proximally. As translatable members (361) are driven proximally, tension is communicated to articulation bands (140, 142) to increase the rigidity of articulation section (130) by taking up any slack that might otherwise exist in articulation section (130). It should be understood that, in the present example, knob (320) may be pivoted to the position shown in FIG. 14 only when articulation section (130) is in a straight, non-articulated configuration. Some other versions may permit knob (320) to be pivoted to the position shown in FIG. 14 when articulation section (130) is in an articulated configuration.

With knob (320) pivoted to a fully pivoted position shown in FIG. 14, articulation bands (140, 142) are in a tensioned configuration and articulation section (130) is correspondingly in a rigid configuration. Once knob (320) is pivoted to the fully pivoted position, an operator may optionally lock knob (320) in the fully pivoted position by transitioning knob lock (315) back to the locked position. However, unlike the locking configuration described above, in this configuration knob lock (315) engages at least a portion of knob (320) to maintain knob (320) in the fully pivoted position. It should be understood that in some examples, knob (320) comprises openings, indentations, or other features that receive a portion of knob lock (314), thereby permitting knob lock (315) to engage knob (320).

Figure 15:
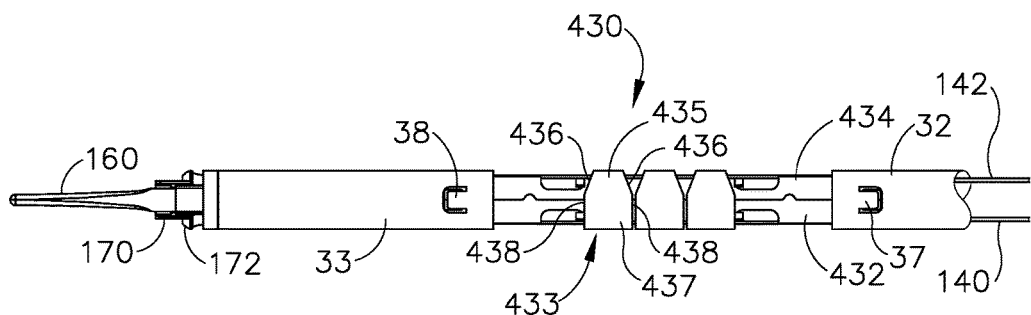
FIG. 15 depicts a top plan view of an exemplary alternative articulation section that may be incorporated into the instrument of FIG. 1, with the articulation section in a straight configuration.
Figure 16:
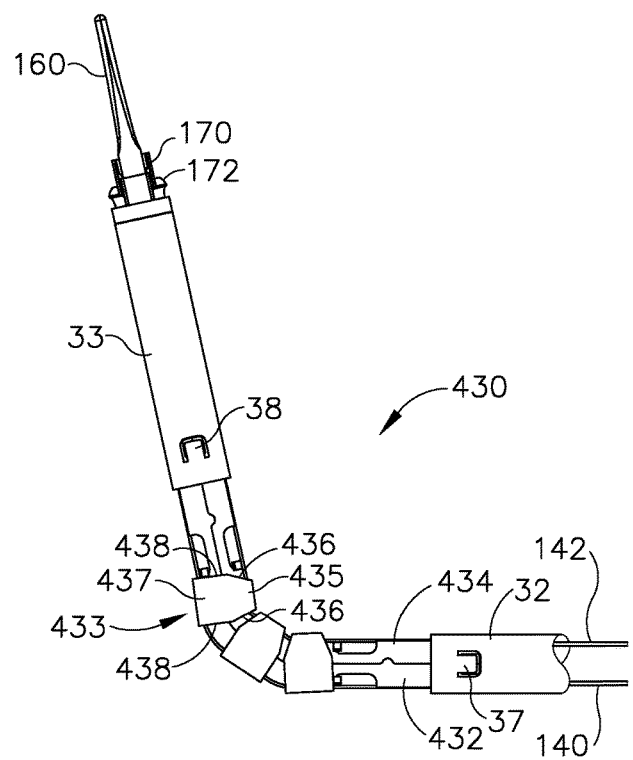
FIG. 16 depicts another top plan view of the articulation section of FIG. 15, with the articulation section in an articulated configuration.

C. Exemplary Alternative Articulation Section with Asymmetrical Retention Collars FIGS. 15 and 16 show an exemplary alternative articulation section that may be readily incorporated into instrument (10). It should be understood that unless otherwise described herein, articulation section (430) is substantially the same as articulation section (130) described above. For instance, like articulation section (130), articulation section (430) comprises a pair of ribbed body portions (432, 434) surrounding flexible portion (166) of waveguide (180). Similarly, ribbed body portions (432, 434) are configured to flex with flexible portion (466) of waveguide (180) when articulation section (430) bends to achieve an articulated state.

Also like articulation section (130), articulation section (430) includes a plurality of retention collars (433). Although retention collars (433) of the present example are configured to surround ribbed body portions (432, 434) and are configured to retain articulation bands (140, 142), retention collars (433) are also generally configured for the purpose of providing rigidity to articulation section (430). As can best be seen in FIG. 15, retention collars (433) of the present example are generally wider compared to retention collars (133). With such a width, it should be understood that retention collars (433) substantially abut each other. Each retention collar (433) is asymmetrical and comprises an articulating portion (435) and a locking portion (437). Each articulating portion (435) comprises a chamfered edge (436) on each side of each articulating portion (435). As will be described in greater detail below, each chamfered edge (436) is generally at an oblique angle suitable to permit articulation of articulation section (430). In some examples, each chamfered edge (436) is at an angle of about 15° relative to the longitudinal axis of each retention collar (433), although any other suitable angle may be used.

Each locking portion (437) is generally square or rectangular in shape. Accordingly, each locking portion (437) forms a generally straight edge (438) positioned adjacent to each chamfered edge (436) of each articulating portion (435). As will be understood, each straight edge (438) is generally configured to maintain rigidity of articulation section (430) in a given direction when each retention collar (433) is adjacent to the others.

FIGS. 15 and 16 show an exemplary operation of articulation section (430). As can be seen in FIG. 15, articulation section (430) is generally both unidirectionally rigid and unidirectionally articulable. For instance, if a transversely oriented force is applied to the distal portion of shaft assembly (30) in the direction of locking portions (437) and perpendicular to the longitudinal axis of shaft assembly (30), articulation section (430) resists articulation because each straight edge (438) of each locking portion (437) that is adjacent to another straight edge (438) engages with the other straight edge (438) and thus prevents lateral bending of articulation section (430). Yet, if a transversely oriented force is applied to the distal portion of shaft assembly (300) in the direction of articulating portions (435) and perpendicular to the longitudinal axis of shaft assembly (30), articulation section (430) may be articulated because chamfered edges (436) of each articulating portion (435) provide sufficient clearance to permit lateral bending of articulation section (430).

Although articulating portions (435) permit articulation, it should be understood that articulating portions (435) only permit articulation to the extent that chamfered edges (436) remain away from each other. Once articulation section (430) is articulated to a point where each chamfered edge (436) is adjacent to another, each chamfered edge (436) will act as a physical stop to further articulation similarly to straight edges (438) of each locking portion (437). Thus, both chamfered edges (436) and straight edges (438) act as physical stops that prevent articulation of articulation section (430), but straight edges (438) permit very little to no articulation, while chamfered edges (436) permit a certain predetermined range of articulation. Therefore, if articulation bands (140, 142) are neither in tension nor compression, an operator may apply an articulation force to articulate articulation section (430) in only a single direction and only to a certain predetermined extent. By way of example only, chamfered edges (436) may permit articulation section (430) to achieve an articulation angle of up to approximately 30°.

Alternatively, any other suitable maximum articulation angle may be provided. It should be understood that the "articulation angle" may be an angle defined between the longitudinal axis of distal outer sheath (33) and the longitudinal axis of proximal outer sheath (32).

When an operator desires to lock articulation section (430) in a straight configuration as seen in FIG. 15, a user may place at least articulation band (141) in tension thereby compressing retention collars (433) such that straight edges (438) of locking portions (437) are compressed against each other. While straight edges (438) will prevent articulation in the direction of locking portions (437), tension in articulation band (141) will also prevent articulation in the direction toward articulating portions (435). This is because the tension in articulation band (140) will prevent straight edges (438) from separating relative to each other.

Tension may be applied to articulation band (140) using the articulation control assemblies (110, 210, 310) described above, or any other suitable means. Articulation band (142) may also be placed in tension using the features of articulation assemblies (210, 310) described above, or any other suitable means. Alternatively, articulation band (142) may merely be passive in state with merely no force applied.

When an operator desires to articulate articulation section (430), an operator may release tension from articulation band (140). Once tension is released from articulation band (140), articulation section (430) will be in the passive state described above where articulation is permitted in the direction of articulating portions (435) but not in the direction of locking portions (437). To initiate articulation, an operator may place articulation band (142) in tension while maintaining articulation band (140) in a passive state or actively driving articulation band (140) distally. Tension may be applied to articulation band (140) using articulation control assemblies (110, 210, 310) as described above, or by using any other suitable means. As tension is applied, articulation band (142) generates a moment that bends articulation section (430). Articulation section (430) is then permitted to bend until chamfered edges (436) of articulating portions (435) are adjacent to each other. At such a point chamfered edges (436) begin acting as physical stops as described above thereby preventing further articulation.

Figure 17:
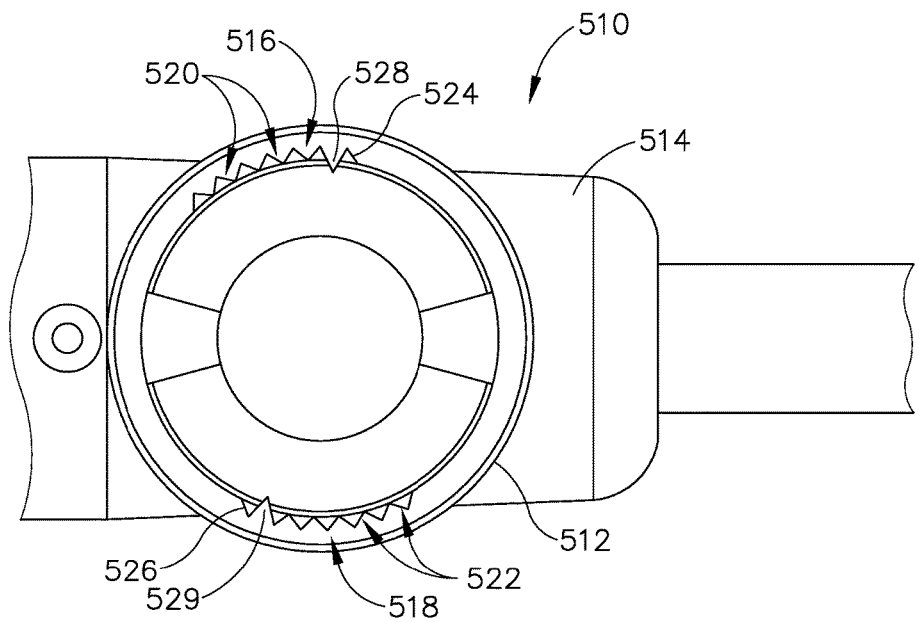
FIG. 17 depicts a top plan view of an exemplary alternative housing that may be incorporated into the instrument of FIG. 1 for use with the articulation section of FIG. 15.

FIG. 17 shows an exemplary alternative housing (510) that may be readily incorporated into instrument (10), particularly when instrument (10) is equipped with articulation section (430) described above. Unless otherwise described herein, it should be understood that housing (510) is substantially the same as housing (110) described above. Additionally, it should be understood that any of the features described herein with respect to housing (510) may be readily incorporated into any housings (110, 210, 310) described above.

Like with housing (110), housing (510) comprises a first cylindrical portion (512) and a second cylindrical portion (514). Second cylindrical portion (514) is substantially the same as second cylindrical portion (114) described above such that further details will not be described herein.

First cylindrical portion (512) is substantially the same as first cylindrical portion (112) described above. For instance, as can be seen in FIG. 17, first cylindrical portion (512) comprises a first angular array of teeth (516) and a second angular array of teeth (518) formed in an interior surface of first cylindrical portion (512). However, unlike teeth (116, 118) described above, teeth (516, 518) of the present example are configured for use with articulation section (430) described above. In particular, each angular array of teeth (516, 518) comprises a respective plurality of articulation teeth (520, 522), a single lock tooth valley (524, 526), and an exaggerated tooth (528, 529) separating the articulation teeth (520, 522) from the lock tooth valley (524, 526).

Each set of articulation teeth (520, 522) functions similarly to teeth (116, 118) described above. For instance, articulation teeth (520, 522) are configured to engage engagement members (126, 128) of rotatable knob (120) such that knob (120) may be rotated to articulate articulation section (430) to a desired position and remain in the same position once any rotational force is removed from knob (120). However, unlike teeth (116, 118), articulation teeth (520, 522) are disposed for movement of articulation section (430) in only a single direction because, as described above, articulation section (430) is only configured for articulation in a single direction.

Each lock tooth valley (524, 526) is configured to hold knob (120) in a position corresponding to a locked position of articulation section (430). It should be understood that each lock tooth valley (524, 526) is disposed in a position corresponding to knob (120) being rotated slightly past a neutral position (e.g., the position aligned with the longitudinal axis of instrument (10)). This positioning ensures that some tension will be applied to actuation band (140) to achieve the locking configuration described above with respect to articulation section (430) while articulation section (430) is in a substantially straight, non-articulated configuration. Although each lock tooth valley (524, 526) of the present example is shown in a given position, it should be understood that the precise position of each lock tooth valley (524, 526) may be varied as desired to achieve a sufficient level of tension in actuation band (140).

Each exaggerated tooth (528, 529) is positioned between each set of actuation teeth (520, 522) and each lock tooth valley (524, 526). Each exaggerated tooth (528, 529) is configured to act as a detent feature that may provide additional support to hold knob (120) in the locked position described above. In particular, each exaggerated tooth (528, 529) is configured to engage engagement members (126, 128) to hold engagement members (126, 128) respective lock tooth valleys (524, 526). Additionally, each exaggerated tooth (528, 529) may act to provide tactile feedback to an operator as knob (120) is transitioned between each set of actuation teeth (520, 522) and each lock tooth valley (524, 526). Although each exaggerated tooth (528, 529) of the present example is shown as having a particular size, it should be understood that the configuration of exaggerated tooth (528, 529) may be varied as desired to achieve suitable detent and/or tactile feedback characteristics.

D. Exemplary Alternative Articulation Section with Articulation Segments

Figure 18:
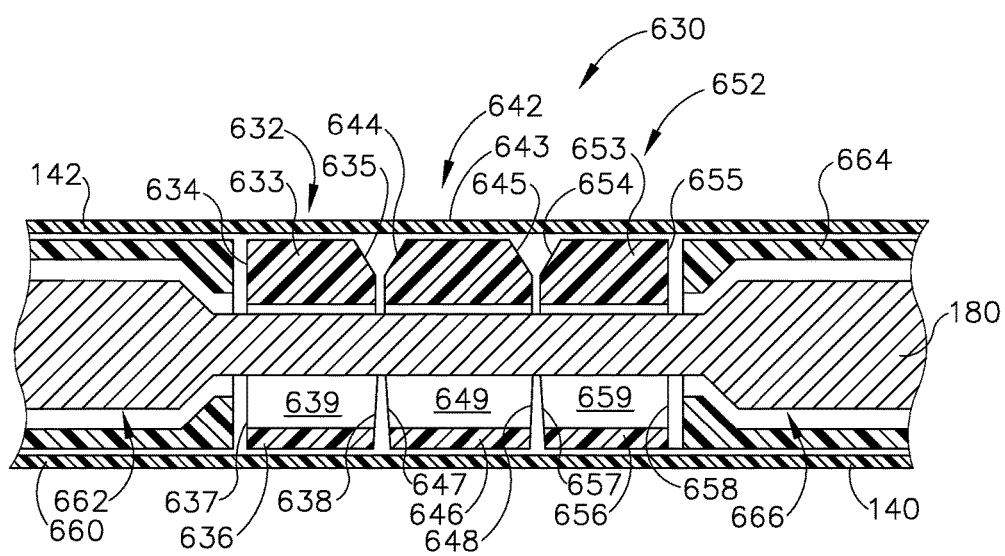
FIG. 18 depicts a top cross-sectional view of another exemplary alternative articulation section that may be incorporated into the instrument of FIG. 1.

FIG. 18 shows another exemplary alternative articulation section (630) that may be readily incorporated into instrument (10). Articulation section (630) comprises three articulation segments (632, 642, 652) disposed between a distal block (660) and a proximal block (664). Articulation segments (632, 642, 652) are configured to operate cooperatively to act as physical stops for different amounts of articulation for a given side of each articulation segment (632, 642, 652). Articulation segments (632, 642, 652) consist of a first articulation segment (632), a second articulation segment (642), and a third articulation segment (652). Although three total articulation segments are shown, it should be understood that in other examples, any suitable number of articulation segments (632, 642, 652) may be used. For instance, in some examples a plurality of second articulation segments (642) may be incorporated between first and third articulation segments (632, 652). In still other examples, second articulation segment (642) may be omitted altogether with first and third articulation segments (632, 652) being adjacent to each other.

First articulation segment (632) includes an articulation portion (633) and a lock portion (636). Articulation portion (633) comprises a straight end (634) disposed adjacent to distal block (660) and a chamfered end (635) disposed adjacent to second articulation segment (642). Straight end (634) is generally straight and is configured to rest squarely against distal block (660). Chamfered end (635) is configured with a chamfer disposed at an angle of approximately 15° relative to the longitudinal axis of first articulation segment (632). As will be described in greater detail below, chamfered end (635) is generally configured to permit articulation of articulation section (630) for a certain amount of articulation (e.g., approximately 30°) before acting as a physical stop.

Lock portion (636) comprises a straight end (637) and a chamfered end (638). Straight end (637) is generally straight and is configured to rest squarely against distal block (660). Chamfered end (638) is configured with a chamfer disposed at an angle of approximately 1° to 5° relative to the longitudinal axis of first articulation segment (632). While chamfered end (638) is configured to permit some articulation of articulation section (630), it should be understood that chamfered end (638) is configured to permit only a limited amount of articulation prior to acting as a physical stop. This is because of the relatively shallow chamfer angle as compared to the chamfer angle of chamfered end (635) described above. Accordingly, as will be described in greater detail below, lock portion (636) generally acts a physical stop for articulation in articulation section (630) despite allowing some relatively limited amount of articulation.

Second articulation segment (642) includes an articulation portion (643) and a lock portion (646). Articulation portion (643) comprises two chamfered ends (644, 645) with a distal chamfered end (644) disposed adjacent to first articulation segment (632) and a proximal chamfered end (645) disposed adjacent to third articulation segment (652). Chamfered ends (644, 645) are generally symmetrical and are both configured with a chamfer disposed at an angle of approximately 15° relative to the longitudinal axis of second articulation segment (642). As will be described in greater detail below, chamfered ends (644, 645) are generally configured to permit articulation of articulation section (630) for a certain amount of articulation (e.g., approximately 30°) before acting as a physical stop.

Lock portion (646) comprises two chamfered ends (647, 648) with a distal chamfered end (647) disposed adjacent to first articulation segment (632) and a proximal chamfered end (648) disposed adjacent to third articulation segment (652). Chamfered ends (637, 638) are both configured with a chamfer disposed at an angle of approximately 1° to 5° relative to the longitudinal axis of second articulation segment (642). While chamfered ends (647, 648) are configured to permit some articulation of articulation section (630), it should be understood that chamfered ends (647, 648) are configured to permit only a limited amount of articulation prior to acting as a physical stop. This is because of the relatively shallow chamfer angle as compared to the chamfer angle of chamfered ends (644, 645) described above. Accordingly, as will be described in greater detail below, lock portion (646) generally acts a physical stop for articulation in articulation section (630) despite allowing some relatively limited amount of articulation.

Third articulation segment (652) is similar to first articulation segment (632) and includes an articulation portion (653) and a lock portion (656). Articulation portion (653) comprises a chamfered end (654) disposed adjacent to second articulation segment (642) and a straight end (655) disposed adjacent to proximal block (664). Chamfered end (654) is configured with a chamfer disposed at an angle of approximately 15° relative to the longitudinal axis of third articulation segment (652). As will be described in greater detail below, chamfered end (654) is generally configured to permit articulation of articulation section (630) for a certain amount of articulation (e.g., approximately 30°) before acting as a physical stop. Straight end (655) is generally straight and is configured to rest squarely against proximal block (664).

Lock portion (656) comprises a chamfered end (657) and a straight end (658). Chamfered end (657) is configured with a chamfer disposed at an angle of approximately 1° to 5° relative to the longitudinal axis of third articulation segment (652). While chamfered end (657) is configured to permit some articulation of articulation section (630), it should be understood that chamfered end (657) is configured to permit only a limited amount of articulation prior to acting as a physical stop. This is because of the relatively shallow chamfer angle as compared to the chamfer angle of chamfered end (654) described above. Accordingly, as will be described in greater detail below, lock portion (656) generally acts a physical stop for articulation in articulation section (630) despite allowing some relatively limited amount of articulation. Straight end (658) is generally straight and is configured to rest squarely against proximal block (664).

Each articulation segment (632, 642, 652) includes a respective bore (639, 649, 659) extending transversely therethrough. Each bore (639, 649, 659) is configured to surround but not contact waveguide (180). For instance, each bore (639, 649, 659) is cut into a larger portion of each respective lock portion (636, 646, 656) relative to each respective articulation portion (633, 643, 653). Because each articulation portion (633, 643, 653) is configured to articulate articulation section (630) a larger amount relative to each lock portion (636, 646, 656), each bore (639, 649, 659) is configured to include additional space on the side of each lock portion (636, 646, 656) to accommodate bending of waveguide (180).

Distal and proximal block (660, 664) each similarly include a respective bore (662, 666) that is configured to surround waveguide (180) without contacting waveguide (180). Additionally, blocks (660, 664) are configured to abut articulation segments (632, 642, 652) and to provide a stable point of contact for segments (632, 642, 652). Although not shown, it should be understood that blocks (660, 664) may also include channels or other features configured to provide a surface for articulation bands (140, 142) to move upon.

In an exemplary mode of operation, an operator may lock articulation section (630) in a generally straight configuration by applying tension to articulation band (140). In particular, tension may be applied using articulation control assemblies (100, 200, 300) as described above. Once tension begins to be applied to articulation band (140), a moment will be created by such tension that will urge chamfered ends (638, 647) of first and second articulation segments (632, 642) toward each other and chamfered ends (648, 657) of second and third articulation segments (642, 652) toward each other until each chamfered end (638, 647, 648, 657) abuts another. Because of the limited chamfer of chamfered ends (638, 647, 648, 657) any articulation of articulation section (630) will be limited at this stage.

Once chamfered ends (638, 647, 648, 657) are abutting, additional articulation will be prevented by physical contact between chamfered ends (638, 647, 648, 657). Thus, while tension is applied to articulation band (140), articulation section (130) will be held in a position of limited to no articulation. It should be understood that the particular amount of articulation of articulation section (630) will be determined by the particular chamfer angles of chamfered ends (638, 647, 648, 657).

When an operator desires to articulate articulation section (630), an operator may first release any tension in articulation band (140). Once tension is released, an operator may apply tension to articulation band (142) using articulation control assembly (100, 200, 300) described above. One tension is applied to articulation band (142), a moment will be created by such tension that will urge chamfered ends (635, 644) of first and second articulation segments (632, 642) toward each other and chamfered ends (645, 654) of second and third articulation segments (642, 652) toward each other until each chamfered end (635, 644, 645, 654) abut another. It should be understood that because of the relatively large chamfer of chamfered ends (635, 644, 645, 654) (compared to chamfered ends (638, 647, 648, 657)), articulation of articulation section (630) about articulation portions (633, 643, 653) will be relatively large in comparison to articulation about lock portions (636, 646, 656). In some examples, such an articulation of articulation section will be approximately 30°.

Once chamfered ends (635, 644, 645, 654) are abutting, additional articulation will be prevented by physical contact between chamfered ends (635, 644, 645, 654). Thus, while tension is applied to articulation band (140), articulation section (130) will be held in an articulated position. It should be understood that the particular amount of articulation of articulation section (630) will be determined by the particular chamfer angles of chamfered ends (635, 644, 645, 654). Accordingly, chamfered ends (635, 644, 645, 654) may be configured to permit any suitable amount of articulation as may be desired.

In one merely illustrative example, a modified version of instrument (10) includes articulation section (630) and housing (510). It should therefore be understood that articulation section (630) may be operated in a manner similar to that described above with respect to articulation section (430). Alternatively, any other suitable control elements may be combined with articulation section (630).

E Exemplary Alternative Instrument with Tensioning Lever

Figure 19:
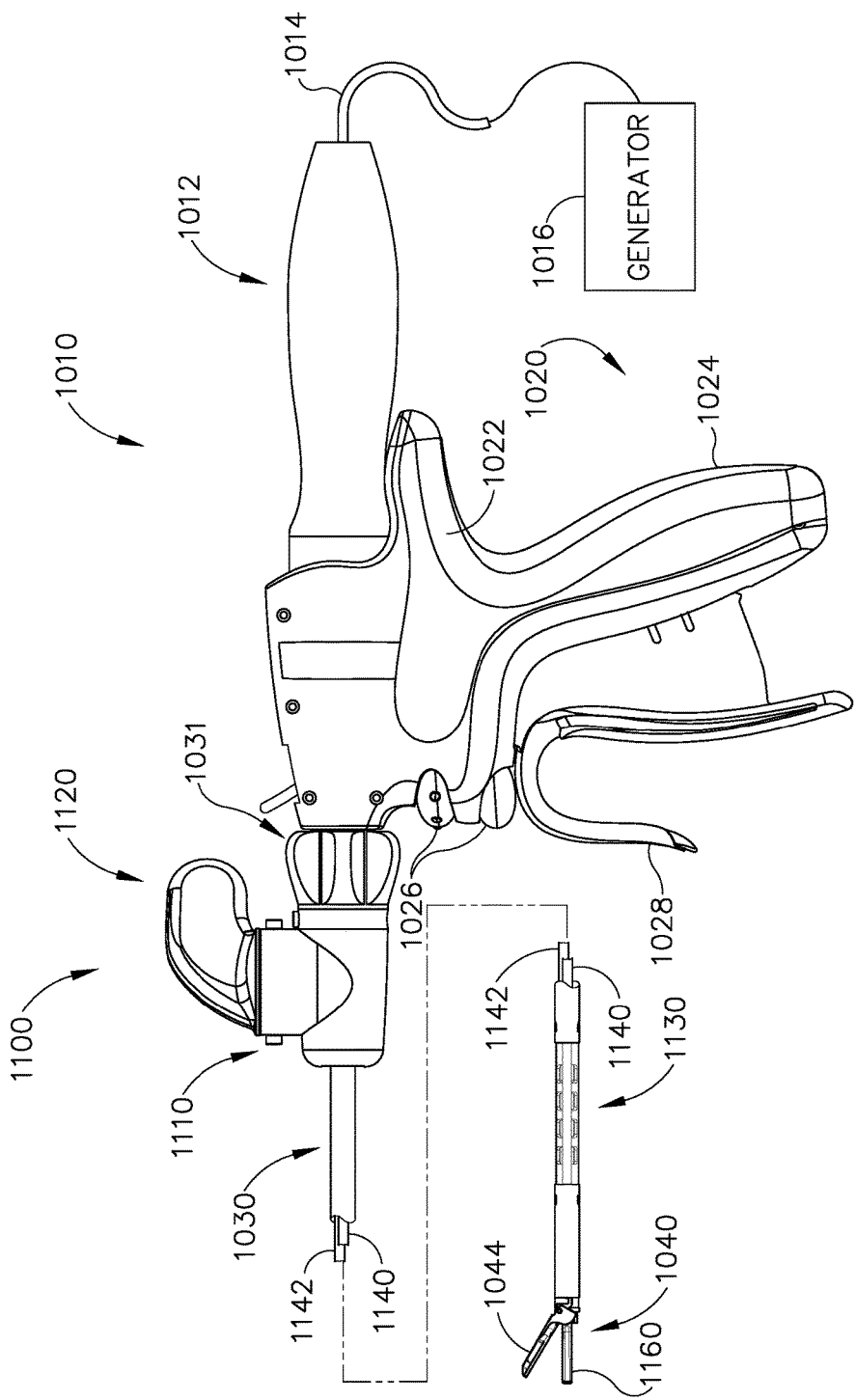
FIG. 19 depicts a side elevational view of an exemplary alternative ultrasonic surgical instrument.

FIG. 19 shows an exemplary alternative instrument (1010). It should be understood that instrument (1010) of the present example is substantially the same as instrument (10) described above, except as otherwise noted herein. For instance, Instrument (1010) of the present example comprises a handle assembly (1020), a shaft assembly (1030), and an end effector (1040). Handle assembly (1020) comprises a body (1022) including a pistol grip (1024) and a pair of buttons (1026). Handle assembly (1020) also includes a trigger (1028) that is pivotable toward and away from pistol grip (1024). It should be understood, however, that various other suitable configurations may be used, including but not limited to a scissor grip configuration. End effector (1040) includes an ultrasonic blade (1160) and a pivoting clamp arm (1044). Clamp arm (1044) is coupled with trigger (1028) such that clamp arm (1044) is pivotable toward ultrasonic blade (1160) in response to pivoting of trigger (1028) toward pistol grip (1024); and such that clamp arm (1044) is pivotable away from ultrasonic blade (1160) in response to pivoting of trigger (1028) away from pistol grip (1024). Various suitable ways in which clamp arm (1044) may be coupled with trigger (1028) will be apparent to those of ordinary skill in the art in view of the teachings herein. In some versions, one or more resilient members are used to bias clamp arm (1044) and/or trigger (1028) to the open position shown in FIG. 1.

An ultrasonic transducer assembly (1012) extends proximally from body (1022) of handle assembly (1020). Transducer assembly (1012) is coupled with a generator (1016) via a cable (1014), such that transducer assembly (1012) receives electrical power from generator (1016). Piezoelectric elements in transducer assembly (1012) convert that electrical power into ultrasonic vibrations. Generator (1016) may include a power source and control module that is configured to provide a power profile to transducer assembly (1012) that is particularly suited for the generation of ultrasonic vibrations through transducer assembly (1012).

Blade (1160) of the present example is operable to vibrate at ultrasonic frequencies in order to effectively cut through and seal tissue. Blade (1160) is positioned at the distal end of an acoustic drivetrain. This acoustic drivetrain includes transducer assembly (1012) and an acoustic waveguide (not shown). The acoustic waveguide comprises a flexible portion (not shown) similar to flexible portion (166) described above with respect to instrument (10). Transducer assembly (1012) includes a set of piezoelectric discs (not shown) located proximal to a horn (not shown) of the waveguide. The piezoelectric discs are operable to convert electrical power into ultrasonic vibrations, which are then transmitted along the waveguide to blade (1160) in accordance with known configurations and techniques. By way of example only, this portion of the acoustic drivetrain may be configured in accordance with various teachings of various references that are cited herein.

Shaft assembly (1030) of the present example extends distally from handle assembly (1020). Unless otherwise noted herein, shaft assembly (1030) is substantially the same as shaft assembly (30) described above with respect to instrument. For instance, shaft assembly (1030) includes an articulation section (1130), which is located at a distal portion of shaft assembly (1030), with end effector (1040) being located distal to articulation section (1130). As shown in FIG. 19, a knob (1031) is secured to a proximal portion of shaft assembly (1030). Knob (1031) is rotatable relative to body (1022), such that shaft assembly (1030) is rotatable about the longitudinal axis defined by shaft assembly (1030), relative to handle assembly (1020). Such rotation may provide rotation of end effector (1040), articulation section (1130), and shaft assembly (1030) unitarily. Of course, rotatable features may simply be omitted if desired.

Articulation section (1130) is substantially the same as articulation section (130) described above with respect to instrument (10), unless otherwise note herein. For instance, articulation section (1130) is operable to selectively position end effector (1040) at various lateral deflection angles relative to a longitudinal axis defined by shaft assembly (1030). Like with articulation section (130), articulation section (1130) is driven by a pair of articulation bands (1140, 1142) disposed within articulation section (1130) and extending through shaft assembly (1030). When articulation bands (1140, 1142) translate longitudinally in an opposing fashion, this will cause articulation section (1130) to bend, thereby laterally deflecting end effector (1040) away from the longitudinal axis of shaft assembly (1030) from a straight configuration to an articulated configuration. In particular, end effector (1040) will be articulated toward the articulation band (1140, 1142) that is being pulled proximally. During such articulation, the other articulation band (1140, 1142) may be pulled or pushed distally Instrument further includes an articulation control assembly (1100) that is secured to a proximal portion of shaft assembly (1030). Articulation control assembly (1100) comprises a housing (1110) and a rotatable knob (1120). Like with articulation control assembly (100) described above, rotatable knob (1120) is configured to rotate relative to housing (1110) to drive articulation bands (1140, 1142) in opposing longitudinal directions. For instance, rotation of knob (1120) in a first direction causes distal longitudinal translation of articulation band (1140), while simultaneously causing proximal longitudinal translation of articulation band (1142). Rotation of knob (1120) in a second direction causes proximal longitudinal translation of articulation band (1140), while simultaneously causing distal longitudinal translation of articulation band (1142). Thus, it should be understood that rotation of rotation knob (1120) causes articulation of articulation section (1130).

Unlike instrument (10) described above, instrument (1010) of the present example further includes a tensioning assembly (1200). Tensioning assembly (1200) is generally operable to translate the entire articulation control assembly (1100) relative to shaft assembly (1030) to thereby simultaneously apply tension to articulation bands (1140, 1142). As can best be seen in FIG. 20, tensioning assembly (1200) comprises a lever arm (1210) and a link (1220). Lever arm (1210) is pivotably secured within handle assembly (1020) and is configured to pivot about a pivot point (1212) connecting lever arm (1210) to housing (1020).

Link (1220) is pivotably connected to lever arm (1210) at a pivot point (1222) connecting link (1220) to lever arm (1210). Link (1220) extends from lever arm (1210) through handle assembly (1020) and through knob (1031) where link (1220) pivotably connects to articulation control assembly (1100). Although not shown, it should be understood that link (1220) may connect to articulation control assembly (1100) by any suitable means. For instance, in some examples link (1220) is connected to articulation control assembly (1100) by a rotatable collar assembly that is configured to permit articulation control assembly (1100) to rotate relative to link (1220) while still permitting link (1220) to drive translation of articulation control assembly (1100). In other examples, link (1220) may simply be integral with articulation control assembly (1100) or connected with a pin or other securing feature. Of course any other suitable mechanisms for connecting link (1220) to articulation control assembly (1100) as will be apparent to those of ordinary skill in the art in view of the teachings herein.

Figure 21:
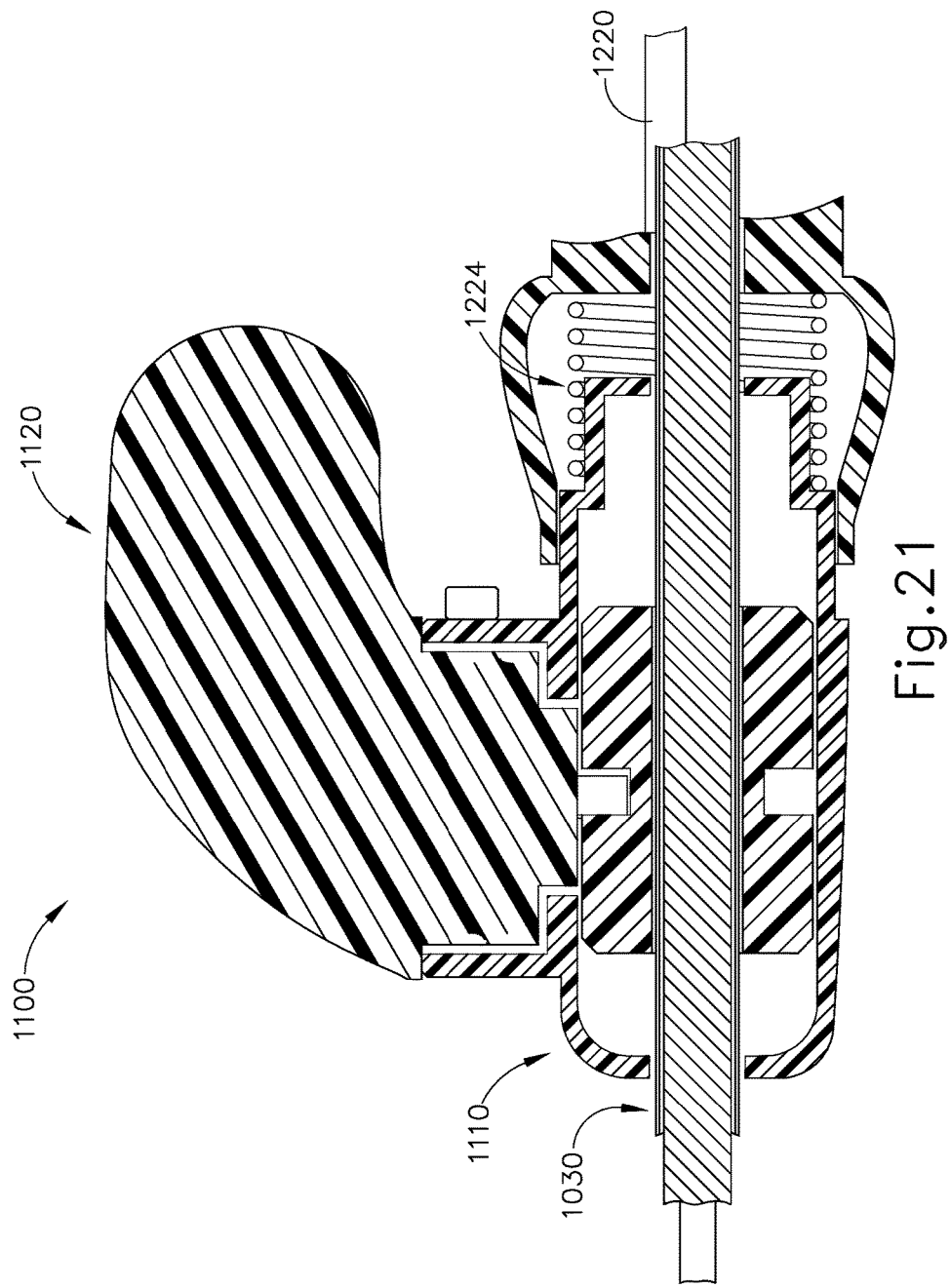
FIG. 21 depicts a side cross-sectional view of a articulation control assembly of the instrument of FIG. 19.

As can best be seen in FIG. 21, articulation control assembly (1100) is configured to translate relative to knob (1031) and shaft assembly (1030). In particular, a proximal portion of housing (1110) is translatably received within knob (1031) to permit some translation of articulation control assembly (1100) relative to knob (1031). Additionally, a spring (1224) is disposed between articulation control assembly (1100) and knob (1031) to resiliently bias articulation control assembly (1100) toward a distal position. As will be described in greater detail below, the distal position of articulation control assembly (1100) corresponds to an articulation position, where articulation bands (1140, 1142) are subjected to low tension, such that articulation control assembly (1100) may cause articulation section (1130) to articulate.

Figure 20:
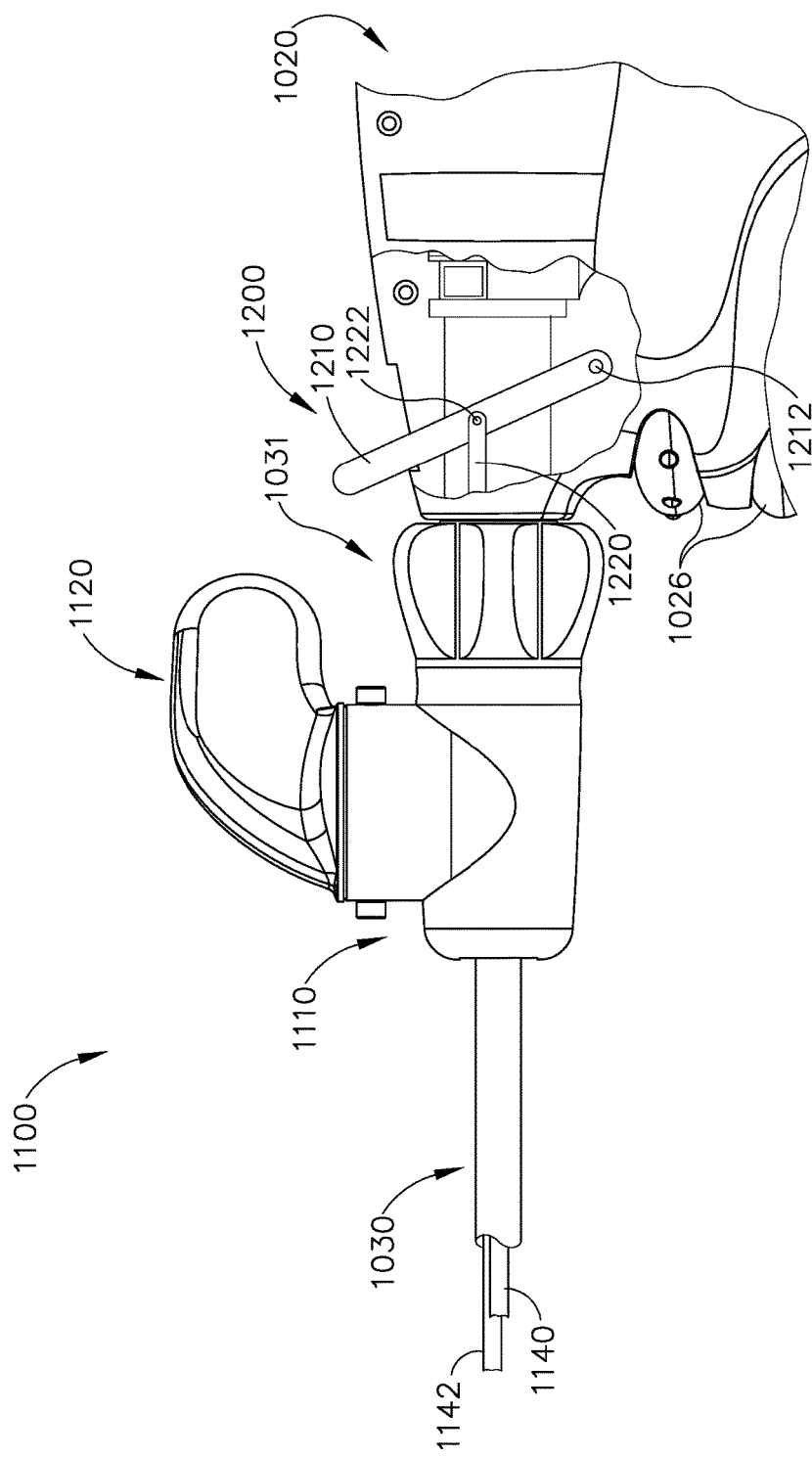
FIG. 20 depicts a detailed side cut-away view of the instrument of FIG. 19, with a tensioning assembly in a non-tensioning position.
Figure 22:
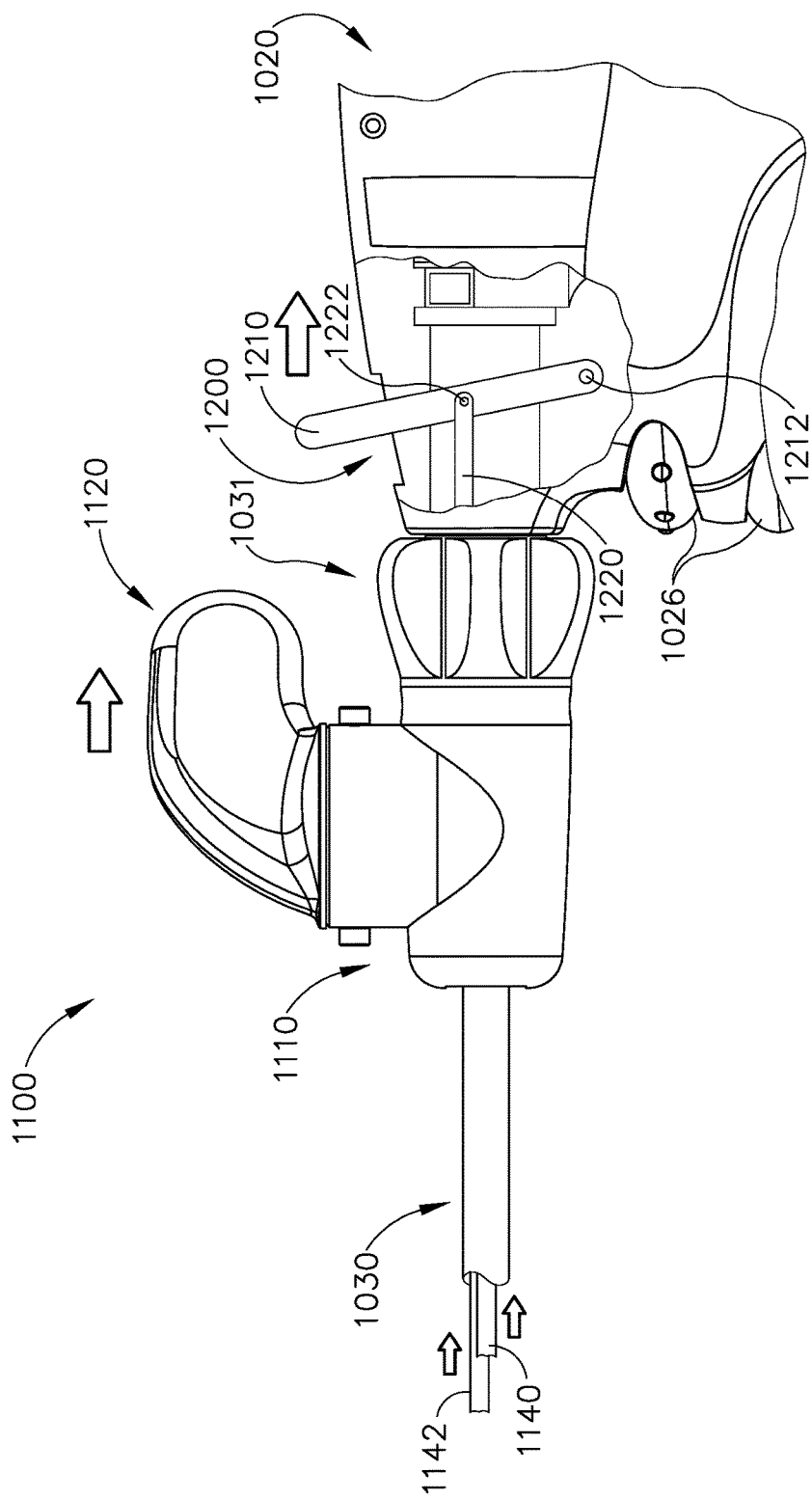
FIG. 22 depicts a detailed side cut-away view of the instrument of FIG. 19, with a tensioning assembly in a tensioned position.

FIGS. 20 and 22 show an exemplary mode of operation of tensioning assembly (1200). In particular, FIG. 20 shows tensioning assembly (1200) in an articulation position. Generally, the articulation position corresponds to articulation bands (1140, 1142) being in a low tension state such that knob (1120) of articulation control assembly (1100) may be used to drive articulation bands (1140, 1142) in opposing directions to articulate articulation section (1130). In the articulation position, lever arm (1210) is pivoted distally relative to handle assembly (1020). Because link (1220) is attached to lever arm (1210), link (1220) is also positioned distally to thereby permit spring (1224) to drive articulation control assembly (1100) distally.

An operator may desire to increase the rigidity of articulation section (1130) to thereby lock articulation section (1130) in a particular state of articulation (e.g., straight). To do so, it may be desirable to simultaneously apply tension to both articulation bands (1140, 1142) because such tension may provide opposing forces on articulation section (1130) that work to maintain articulation section (1130) in a given position. To simultaneously tension both articulation bands (1140, 1142), an operator may grasp lever arm (1210) and pull lever arm (1210) proximally relative to handle assembly (1020).

As can be seen in FIG. 22, pulling lever arm (1210) proximally causes link (1220) to act on articulation control assembly (1100) to thereby translate articulation control assembly (1100) proximally relative to knob (1031). Because articulation bands (1140, 1142) are both connected to articulation control assembly (1100), such translation will simultaneously increase tension each articulation band (1140, 1142). This tension will be transferred to the movable components within articulation section (1130), thereby taking up any slack that might otherwise exist within articulation section (1130). Once tension is applied to articulation bands (1140, 1142), the particular articulation state of articulation section (1130) (e.g., straight) will thus correspondingly be locked.

In some examples, tensioning assembly (1200) may include a lock feature or other mechanism to selectively maintain lever arm (1210) in the tensioned position. Where such features are included, an operator may actuate such features after lever arm (1210) is positioned to tension articulation bands (1140, 1142). As another merely illustrative example, lever arm (1210) and link (1220) may be configured to provide an over-center toggle mechanism, such as the over-center toggle described below. Alternatively, locking features may be omitted and lever arm (1210) may simply return to the articulation position once an operator releases lever arm (1210), due to the resilience of spring (1224).

F. Exemplary Alternative Instrument with Over-Center Toggle Tensioning Assembly

Figure 23:
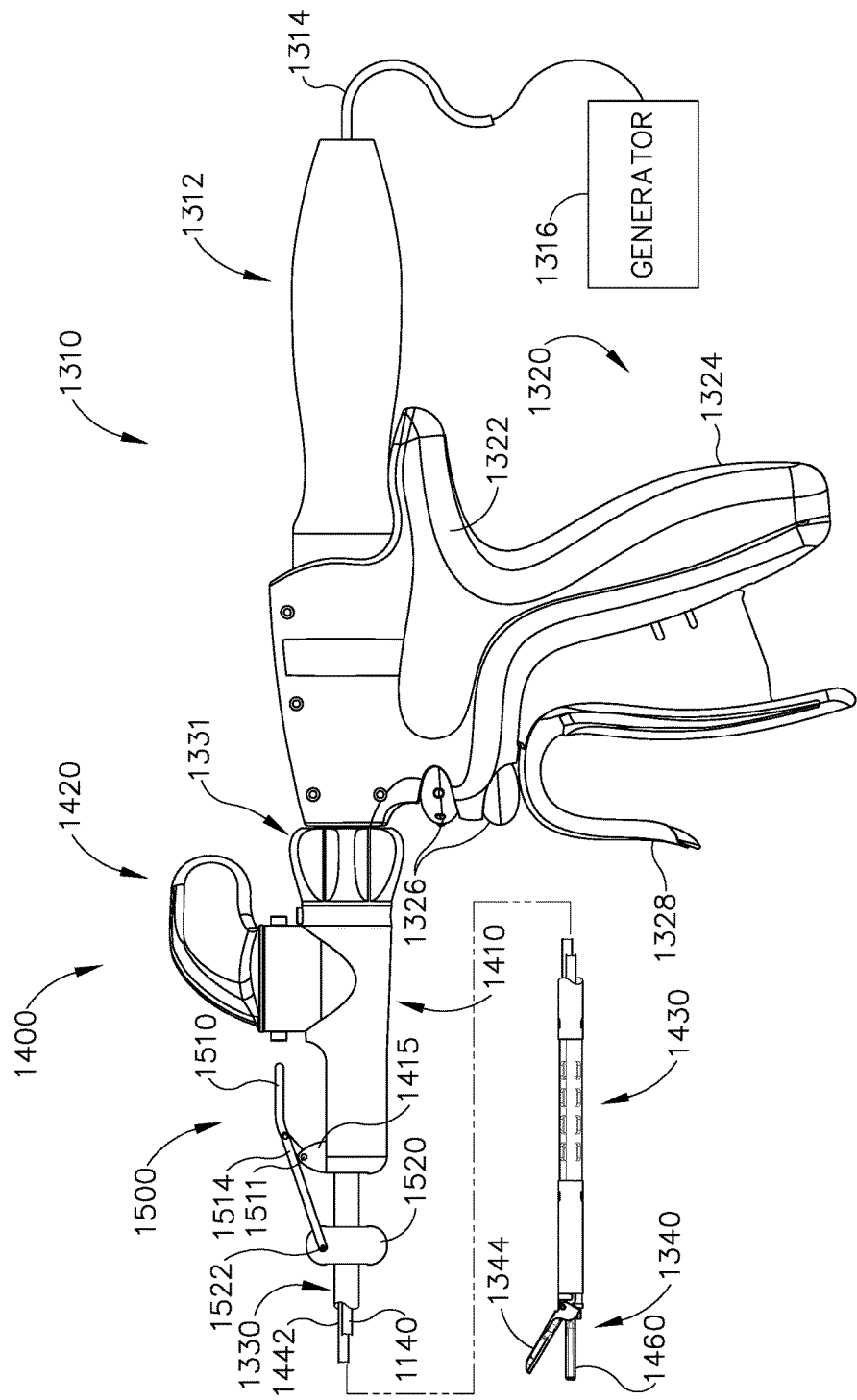
FIG. 23 depicts a side elevational view of another exemplary alternative surgical instrument.

FIG. 23 shows an exemplary alternative instrument (1310). It should be understood that instrument (1310) of the present example is substantially the same as instrument (10) described above, except as otherwise noted herein. For instance, Instrument (1310) of the present example comprises a handle assembly (1320), a shaft assembly (1330), and an end effector (1340). Handle assembly (1320) comprises a body (1322) including a pistol grip (1324) and a pair of buttons (1326). Handle assembly (1320) also includes a trigger (1328) that is pivotable toward and away from pistol grip (1324). It should be understood, however, that various other suitable configurations may be used, including but not limited to a scissor grip configuration. End effector (1340) includes an ultrasonic blade (1460) and a pivoting clamp arm (1344). Clamp arm (1344) is coupled with trigger (1328) such that clamp arm (1344) is pivotable toward ultrasonic blade (1460) in response to pivoting of trigger (1328) toward pistol grip (1324); and such that clamp arm (1344) is pivotable away from ultrasonic blade (1460) in response to pivoting of trigger (1328) away from pistol grip (1324). Various suitable ways in which clamp arm (1344) may be coupled with trigger (1328) will be apparent to those of ordinary skill in the art in view of the teachings herein. In some versions, one or more resilient members are used to bias clamp arm (1344) and/or trigger (1328) to the open position shown in FIG. 23.

An ultrasonic transducer assembly (1312) extends proximally from body (1322) of handle assembly (1320). Transducer assembly (1312) is coupled with a generator (1316) via a cable (1314), such that transducer assembly (1312) receives electrical power from generator (1316). Piezoelectric elements in transducer assembly (1312) convert that electrical power into ultrasonic vibrations. Generator (1316) may include a power source and control module that is configured to provide a power profile to transducer assembly (1312) that is particularly suited for the generation of ultrasonic vibrations through transducer assembly (1312).

Blade (1460) of the present example is operable to vibrate at ultrasonic frequencies in order to effectively cut through and seal tissue. Blade (1460) is positioned at the distal end of an acoustic drivetrain. This acoustic drivetrain includes transducer assembly (1312) and an acoustic waveguide (not shown). The acoustic waveguide comprises a flexible portion (not shown) similar to flexible portion (166) described above with respect to instrument (10). Transducer assembly (1312) includes a set of piezoelectric discs (not shown) located proximal to a horn (not shown) of the waveguide. The piezoelectric discs are operable to convert electrical power into ultrasonic vibrations, which are then transmitted along the waveguide to blade (1460) in accordance with known configurations and techniques. By way of example only, this portion of the acoustic drivetrain may be configured in accordance with various teachings of various references that are cited herein.

Shaft assembly (1330) of the present example extends distally from handle assembly (1320). Unless otherwise noted herein, shaft assembly (1330) is substantially the same as shaft assembly (30) described above with respect to instrument. For instance, shaft assembly (1330) includes an articulation section (1430), which is located at a distal portion of shaft assembly (1330), with end effector (1340) being located distal to articulation section (1430). As shown in FIG. 23, a knob (1331) is secured to a proximal portion of shaft assembly (1330). Knob (1331) is rotatable relative to body (1322), such that shaft assembly (1330) is rotatable about the longitudinal axis defined by shaft assembly (1330), relative to handle assembly (1320). Such rotation may provide rotation of end effector (1340), articulation section (1430), and shaft assembly (1330) unitarily. Of course, rotatable features may simply be omitted if desired.

Articulation section (1430) is substantially the same as articulation section (130) described above with respect to instrument (10), unless otherwise note herein. For instance, articulation section (1430) is operable to selectively position end effector (1340) at various lateral deflection angles relative to a longitudinal axis defined by shaft assembly (1430). Like with articulation section (130), articulation section (1430) is driven by a pair of articulation bands (1440, 1442) disposed within articulation section (1430) and extending through shaft assembly (1330). When articulation bands (1440, 1142) translate longitudinally in an opposing fashion, this will cause articulation section (1430) to bend, thereby laterally deflecting end effector (1340) away from the longitudinal axis of shaft assembly (1330) from a straight configuration to an articulated configuration. In particular, end effector (1340) will be articulated toward the articulation band (1440, 1442) that is being pulled proximally. During such articulation, the other articulation band (1440, 1442) may be pulled or pushed distally Instrument further includes an articulation control assembly (1400) that is secured to a proximal portion of shaft assembly (1330). Articulation control assembly (1400) comprises a housing (1410) and a rotatable knob (1420). Like with articulation control assembly (100) described above, rotatable knob (1420) is configured to rotate relative to housing (1410) to drive articulation bands (1440, 1442) in opposing longitudinal directions. For instance, rotation of knob (1420) in a first direction causes distal longitudinal translation of articulation band (1440), while simultaneously causing proximal longitudinal translation of articulation band (1442). Rotation of knob (1420) in a second direction causes proximal longitudinal translation of articulation band (1440), while simultaneously causing distal longitudinal translation of articulation band (1442). Thus, it should be understood that rotation of rotation knob (1420) causes articulation of articulation section (1430).

Unlike instrument (10) described above, instrument (1310) of the present example further includes a tensioning assembly (1500). Tensioning assembly (1500) is generally operable as a over-center toggle mechanism to directly apply tension to articulation bands (1440, 1442) and to maintain such tension. In particular, as can best be seen in FIGS. 23 and 24, tensioning assembly (1500) comprises a lever arm (1510) and a collar (1520) disposed about shaft assembly (1330). Lever arm (1510) is attached to housing (1410) of actuation control assembly (1400) at an integral attachment yoke (1415) of housing (1410). Lever arm (1510) is connected to attachment yoke (1415) via a pin (1511) that is configured to permit lever arm (1510) to pivot relative to attachment yoke (1415). As will be described in greater detail below, lever arm (1510) is generally configured to pivot relative to attachment yoke (1415) as an over-center toggle mechanism to drive collar (1520) proximally or distally.

Lever arm (1510) is connected to collar (1520) by two links (1512, 1514) extending between lever arm (1510) and collar (1520). Each link (1512, 1514) is pivotably connected to lever arm at a pin (1515) disposed near the center of lever arm (1510). Each link (1512, 1514) also pivotably connects to collar (1520) at a respective pivotal coupling (1521, 1522). Both pin (1515) and pivotal couplings (1521, 1522) allow each link to pivot as lever arm (1510) and collar (1520) are moved.

Figure 24:
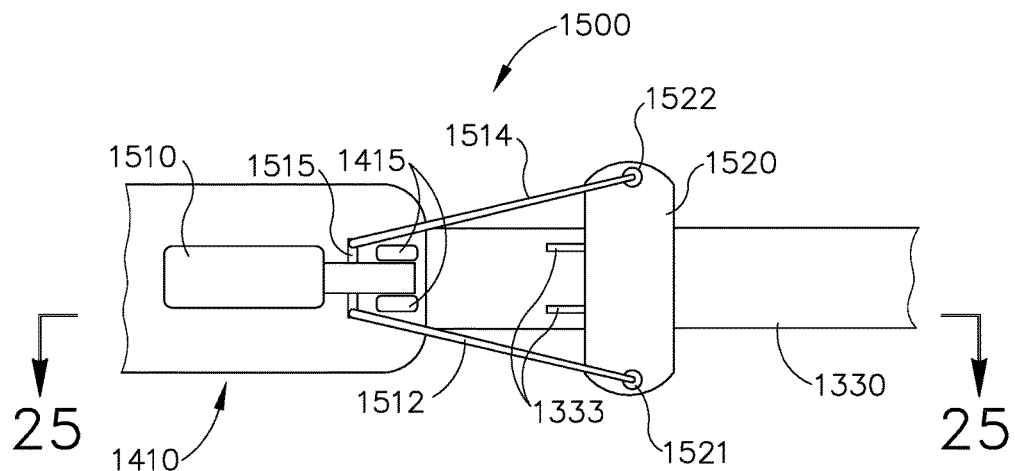
FIG. 24 depicts a detailed top plan view of a tensioning assembly of the instrument of FIG. 23.
Figure 25:
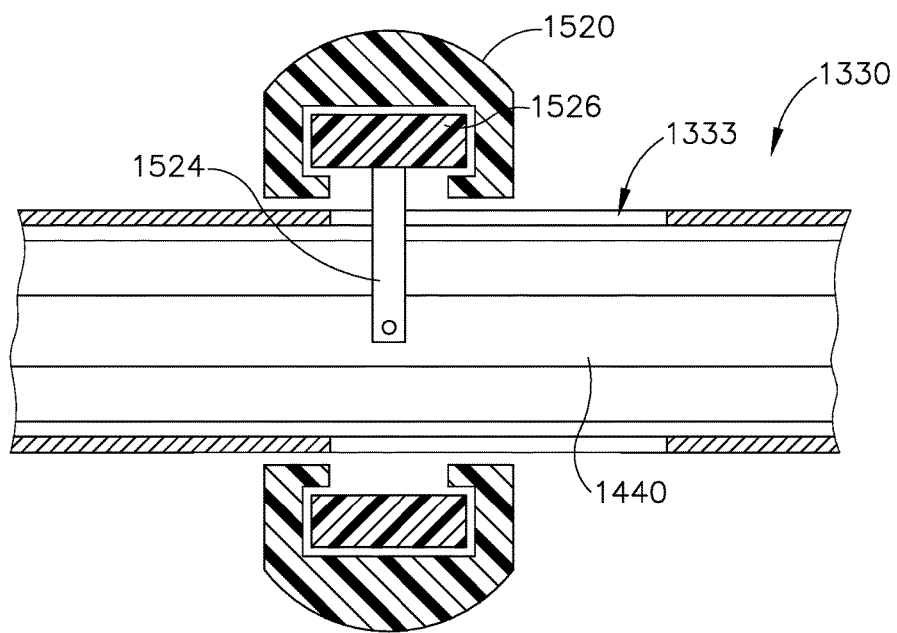
FIG. 25 depicts a side cross-sectional view of a collar of the tensioning assembly of FIG. 24, with the cross-section taken along line 25-25 of FIG. 24.

As can best be seen in FIGS. 24 and 25, collar (1520) includes a pair of inwardly extending armatures (1524) (only a single armature is shown) that extend from collar (1520) and into shaft assembly (1330) through a pair of slots (1333) in shaft assembly (1330). Each armature (1524) connects to a respective articulation band (1440, 1442). In particular, each articulation band (1440, 1442) includes a slot that receives a corresponding armature (1524). The slots and armatures (1524) are configured such that articulation bands (1440, 1442) may move freely in opposing longitudinal directions when collar (1520) is in the distal position shown in FIG. 26. However, when collar (1520) is moved to the proximal position shown in FIG. 27 as described in greater detail below, the and armatures (1524) are configured such that armatures (1524) reach the proximal ends of those slots, thereby pulling proximally on articulation bands (1440, 1442) to provide tension in articulation bands (1440, 1442). The opposite end of each armature (1524) is integral or fixedly secured to an inner ring (1526) disposed within collar (1520) Inner ring (1526) is configured to freely rotate within collar (1520) while still transferring any translation of collar (1520) to each armature (1524). Such a feature may be desirable because when collar (1520) includes such a feature, collar (1520) may remain stationary while shaft assembly (1330) is rotated.

As another exemplary configuration, collar (1520) may include a cam feature that provides selective engagement between collar (1520) and articulation bands (1440, 1442). For instance, when such a cam feature is in a first position, collar (1520) may be disengaged from articulation bands (1440, 1442), such that articulation bands (1440, 1442) may move freely in opposing longitudinal directions when the cam feature is in the first position. When the cam feature is moved (e.g., rotated, slid, etc.) to a second position, the cam feature may provide engagement between collar (1520) and articulation bands (1440, 1442), such that longitudinal motion of collar (1520) provides corresponding, simultaneous longitudinal motion of articulation bands (1440, 1442). Other suitable structures and relationships that may be provided between collar (1520) and articulation bands (1440, 1442) will be apparent to those of ordinary skill in the art in view of the teachings herein.

Figure 26:
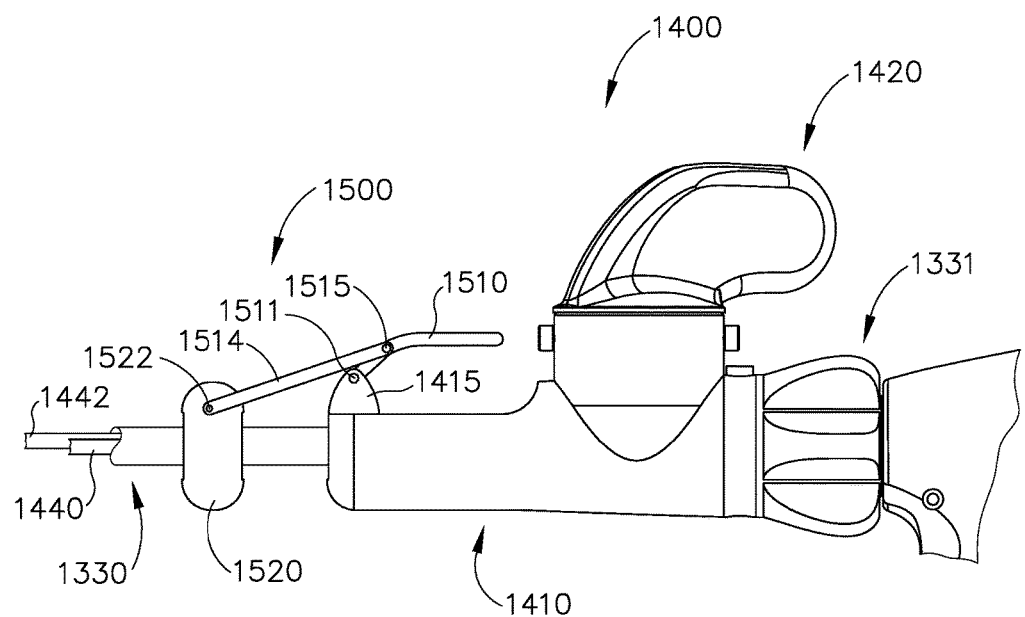
FIG. 26 depicts a detailed side elevational view of the tensioning assembly of FIG. 24, with the tensioning assembly in a non-tensioning position.
Figure 27:
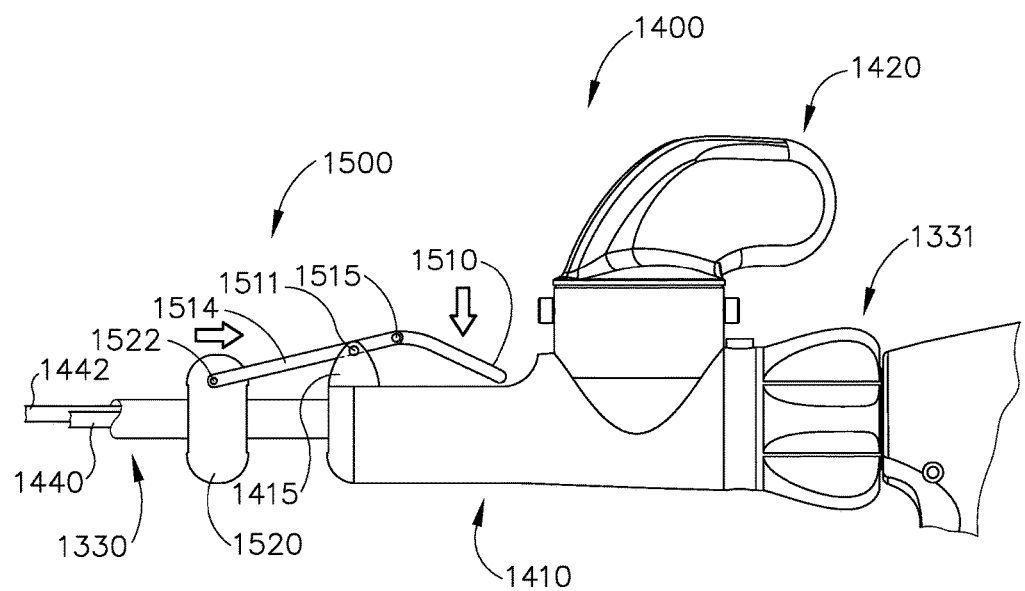
FIG. 27 depicts another detailed side elevational view of the tensioning assembly of FIG. 24, with the tensioning assembly in a tensioning position.

An exemplary use of tensioning assembly (1500) is shown in FIGS. 26 and 27. In particular, tensioning assembly (1500) may initially be in a non-tensioning or relaxed position. In such a position, lever arm (1510) is pivotably disposed upwardly such that pin (1515) is disposed above pin (1511). With lever arm (1510) positioned upwardly, collar (1520) is pushed to a distal position relative to shaft assembly (1330) by each link (1512, 1514). Because collar (1520) is attached to articulation bands (1440, 1442) via armatures (1524), articulation bands (1440, 1442) are in a non-tensioned or relaxed state when collar (1520) is in the distal position. Accordingly, articulation bands (1440, 1442) may be used to articulate articulation section (1430) via articulation control assembly (1400) as described above when collar (1520) is in the distal position.

To transition tensioning assembly (1500) to a tensioning position, an operator may pivot lever arm (1510) downwardly to the position shown in FIG. 27. As can be seen, when lever arm (1510) is forced downwardly, each link (1512, 1514) pulls collar (1520) proximally relative to shaft assembly (1330). Because collar (1520) is attached to each articulation band (1440, 1442), collar (1520) will simultaneously pull each articulation band (1440, 1442) correspondingly proximally. Thus, collar (1520) will act to apply tension to each articulation band (1440, 1442) as it is pulled proximally by lever arm (1510).

With lever arm (1510) in the position shown in FIG. 27, tensioning assembly (1500) is in a tensioned position. In the tensioned position, collar (1520) is at its furthest proximal position relative to shaft assembly (1330) and articulation bands (1440, 1442) are correspondingly fully tensioned. Additionally, lever arm (1510) is positioned such that pin (1515) is disposed below pin (1511). Because of this and the tensioning force generated between lever arm (1510) and collar (1520), lever arm (1510) is generally fixed in the tensioned position, such that tensioning assembly (1500) provides an over-center toggle. Accordingly, should an operator desire to return tensioning assembly (1500) to the non-tensioning or relaxed position, the operator will need to pivot lever arm (1510) upwardly back to the position shown in FIG. 23. While the present example includes an over-center toggle feature to maintain lever arm (1510) in the tensioned position, any other suitable feature or mechanism may be used. Alternatively, in other examples such a feature may simply be omitted.

In one some alternative versions of instrument (1400), collar (1520) is omitted. In some such versions, yoke (1415) is an integral feature of body (1322) of handle assembly (1320), such that lever arm (1510) is pivotably coupled directly to handle assembly (1320). In addition, in some such versions, the distal ends of links (1512, 1514) are pivotably coupled directly with housing (1410) of articulation control assembly (1400). Such an example may operate similar to the example of instrument (1100) described above. Thus, when lever arm (1510) is pivoted to an upward position, articulation control assembly (1400) is in a distal position and articulation bands (1440, 1442) are free to translate in order to provide articulation of articulation section (1430). When lever arm (1510) is pivoted to a downward position, articulation control assembly (1400) is in a proximal assembly, pulling articulation bands (1440, 1442) such that articulation bands (1440, 1442) are in tension, thereby effectively rigidizing articulation section (1430) (e.g., when articulation section is in a straight or non-articulated state). Other suitable variations will be apparent to those of ordinary skill in the art in view of the teachings herein.

III. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a first member, and (ii) a second member, wherein the second member is longitudinally translatable relative to the first member; (e) an end effector comprising an ultrasonic blade in acoustic communication with the waveguide; and (f) an articulation lock, wherein the articulation lock comprises a tensioning feature, wherein the tensioning feature is configured to selectively apply tension to at least one of the first member and the second member of the articulation section to thereby increase rigidity in the articulation section.

Example 2

The apparatus of Example 1 or any of the following examples, wherein the tensioning feature of the articulation lock is configured to selectively apply tension to both the first member and the second member of the articulation section.

Example 3

The apparatus of Example 2, further comprising an articulation control assembly in communication with the first member and the second member of the articulation section.

Example 4

The apparatus of Example 3, wherein the tensioning feature of the articulation lock is configured to drive the articulation control assembly proximally to apply tension to both the first member and the second member of the articulation section.

Example 5

The apparatus of Example 3, wherein the articulation control assembly comprises a knob, wherein the knob is configured to rotate to drive the first member and second member of the articulation section in opposing directions.

Example 6

The apparatus of Example 5, wherein the knob is configured to translate to drive both the first member and the second member of the articulation section simultaneously in the same direction.

Example 7

The apparatus of Example 6, wherein the tensioning feature comprises two chamfered members extending from the knob, wherein the chamfered members are operable to apply tension to both the first member and the second member of the articulation section.

Example 8

The apparatus of Example 5, wherein the knob is configured to pivot to drive both the first member and the second member of the articulation section in the same direction, wherein the tensioning feature of the articulation lock comprises two pins extending from the knob.

Example 9

The apparatus of any of the preceding or following Examples, wherein the articulation lock includes at least two asymmetrical segments disposed adjacent to teach other on the articulation section.

Example 10

The apparatus of Example 9, wherein each asymmetrical segment comprises an articulation portion and a lock portion, wherein the articulation portion includes a chamfer, wherein the lock portion is straight relative to the chamfer of the articulation portion.

Example 11

The apparatus of Example 10, wherein the first member is adjacent to the articulation portion, wherein the second member is adjacent to the lock portion, wherein the tensioning feature is configured to selectively apply tension to the first member to articulate the articulation section in the direction of the articulation portion of each asymmetrical segment.

Example 12

The apparatus of Example 11, wherein the tensioning feature is configured to selectively apply tension to the second member to render the articulation section rigid by abutting the lock portions of each asymmetrical link with the other adjacent asymmetrical segments.

Example 13

The apparatus of any of the preceding or following Examples, wherein the articulation lock further comprises a lever, wherein the tensioning feature includes a collar disposed around at least a portion of the shaft, wherein the lever is in communication with the collar via at least one link.

Example 14

The apparatus of Example 13, wherein the lever comprises a first armature and a second armature extending into the shaft from the collar, wherein the first armature is secured to the first member of the articulation section, wherein the second armature is secured to the second member of the articulation section.

Example 15

The apparatus of Example 14, wherein the lever is configured to translate the collar relative to the shaft to a tensioning position, wherein the collar is configured to apply tension to the first and second members of the articulation section when the collar is disposed in the tensioning position.

Example 16

The apparatus of Example 15, wherein the lever comprises an over-center toggle mechanism.

Example 17

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises a working element configured to engage tissue; (e) an articulation drive assembly operable to drive articulation of the articulation section to thereby deflect the end effector from the longitudinal axis, wherein the articulation drive assembly comprises: (i) a first translating driver, and (ii) a second translating driver; and (f) an articulation lock assembly, wherein the articulation lock assembly is in communication with at least one of the first translating driver and the second translating driver.

Example 18

The apparatus of Example 17, wherein the articulation lock assembly is configured to selectively transition the articulation section between a locked configuration and an articulatable configuration.

Example 19

The apparatus of Example 18, wherein the articulation lock assembly is configured to simultaneously place the first translating driver and the second translating driver in tension to thereby transition the articulation section into the locked configuration.

Example 20

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section; (e) a first pair of translating members, wherein the first pair of translating members is operable to actuate the articulation section to thereby deflect the end effector from the longitudinal axis; (f) a drive assembly in communication with the first pair of translating members, wherein the drive assembly is configured to translate the first pair of translating members to actuate the articulation section; and (g) a tensioning assembly, wherein the tensioning assembly is in configured to transition between a first configuration and a second configuration, wherein the tensioning assembly is configured to render the articulation section rigid when in the tensioning assembly is in the first configuration.

IV. MISCELLANEOUS

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body assembly;
   (b) a shaft extending distally from the body assembly, wherein the shaft defines a longitudinal axis;
   (c) an acoustic waveguide, wherein the waveguide comprises a flexible portion;
   (d) an articulation section coupled with the shaft, wherein a portion of the articulation section encompasses at least a portion of the flexible portion of the waveguide, wherein the articulation section further comprises:
      (i) a first member, and
      (ii) a second member, wherein the second member is longitudinally translatable relative to the first member;
   (e) an end effector comprising an ultrasonic blade in acoustic communication with the waveguide; and
   (f) an articulation lock assembly, wherein a distal portion of the articulation lock assembly encompasses a portion of the flexible portion of the waveguide, wherein a proximal portion of the articulation lock assembly comprises a tensioning feature, wherein the tensioning feature is configured to selectively apply tension to at least one of the first member and the second member of the articulation section to thereby increase rigidity in the articulation section.

2. The apparatus of claim 1, wherein the tensioning feature of the articulation lock assembly is configured to selectively apply tension to both the first member and the second member of the articulation section.

3. The apparatus of claim 2, further comprising an articulation control assembly in communication with the first member and the second member of the articulation section.

4. The apparatus of claim 3, wherein the tensioning feature of the articulation lock assembly is configured to drive the articulation control assembly proximally to apply tension to both the first member and the second member of the articulation section.

5. The apparatus of claim 3, wherein the articulation control assembly comprises a knob, wherein the knob is configured to rotate to drive the first member and second member of the articulation section in opposing directions.

6. The apparatus of claim 5, wherein the knob is configured to translate to drive both the first member and the second member of the articulation section simultaneously in the same direction.

7. The apparatus of claim 6, wherein the tensioning feature comprises two chamfered members extending from the knob, wherein the chamfered members are operable to apply tension to both the first member and the second member of the articulation section.

8. The apparatus of claim 5, wherein the knob is configured to pivot to drive both the first member and the second member of the articulation section in the same direction, wherein the tensioning feature of the articulation lock assembly comprises two pins extending from the knob.

9. The apparatus of claim 1, wherein the articulation lock assembly includes at least two asymmetrical segments disposed adjacent to each other on the articulation section.

10. The apparatus of claim 9, wherein each asymmetrical segment comprises an articulation portion and a lock portion, wherein the articulation portion includes a chamfer, wherein the lock portion is straight relative to the chamfer of the articulation portion.

11. The apparatus of claim 10, wherein the first member is adjacent to the articulation portion, wherein the second member is adjacent to the lock portion, wherein the tensioning feature is configured to selectively apply tension to the first member to articulate the articulation section in the direction of the articulation portion of each asymmetrical segment.

12. The apparatus of claim 11, wherein the tensioning feature is configured to selectively apply tension to the second member to render the articulation section rigid by abutting the lock portions of each asymmetrical link with the other adjacent asymmetrical segments.

13. An apparatus for operating on tissue, the apparatus comprising:
(a) a body assembly;
(b) a shaft extending distally from the body assembly, wherein the shaft defines a longitudinal axis and includes an acoustic waveguide having a flexible portion;
(c) an articulation section coupled with the shaft, wherein the flexible portion of the acoustic waveguide extends through the articulation section;
(d) an end effector fixedly coupled with the articulation section, wherein the end effector comprises a working element configured to engage tissue;
(e) an articulation drive assembly operable to drive articulation of the articulation section to thereby deflect the end effector from the longitudinal axis, wherein the articulation drive assembly comprises:
(i) a first translating driver, and
(ii) a second translating driver; and
(f) an articulation lock assembly, wherein a first portion of the articulation lock assembly is laterally disposed between the first and second translating drivers such that the first and second translating drivers are configured to translate external of the first portion, wherein a second portion of the articulation lock assembly is in communication with at least one of the first translating driver and the second translating driver such that the second portion engages at least one of the first and second translating drivers.

14. The apparatus of claim 13, wherein the articulation lock assembly is configured to selectively transition the articulation section between a locked configuration and an articulatable configuration.

15. The apparatus of claim 14, wherein the articulation lock assembly is configured to simultaneously place the first translating driver and the second translating driver in tension to thereby transition the articulation section into the locked configuration.

16. An apparatus for operating on tissue, the apparatus comprising:
(a) a body assembly;
(b) a shaft extending distally from the body assembly, wherein the shaft defines a longitudinal axis;
(c) an acoustic waveguide, wherein the waveguide comprises a flexible portion;
(d) an articulation section coupled with the shaft, wherein the articulation section encompasses the flexible portion of the waveguide, wherein the articulation section further comprises:
(i) a first member, and
(ii) a second member, wherein the second member is longitudinally translatable relative to the first member;
(e) an end effector coupled with the articulation section, wherein the first and second members are operable to actuate the articulation section to deflect the end effector from the longitudinal axis; and
(f) an articulation lock configured to inhibit deflection of the articulation section in only a single direction such that the articulation section is operable to deflect the end effector in only an opposite direction, wherein the articulation lock further comprises a tensioning feature configured to selectively apply tension to at least one of the first and second members to thereby render the articulation section rigid such that the actuated tensioning feature is configured to inhibit deflection of the articulation section in both directions.

17. The apparatus of claim 1, wherein the body assembly is configured to be grasped by a hand of an operator.

18. The apparatus of claim 17, wherein the body assembly comprises a handle assembly.

19. The apparatus of claim 18, wherein the handle assembly comprises a pistol grip.

* * * * *